US006492498B1

(12) United States Patent
Vallera et al.

(10) Patent No.: US 6,492,498 B1
(45) Date of Patent: Dec. 10, 2002

(54) MULTIMERIC IMMUNOTOXINS

(75) Inventors: Daniel A. Vallera, St. Louis Park, MN (US); Bruce R. Blazar, Golden Valley, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/440,344

(22) Filed: Nov. 15, 1999

(51) Int. Cl.$^{7}$ ................................................ C07K 16/00

(52) U.S. Cl. .................... 530/391.7; 530/300; 530/350; 530/387.1; 424/183.1

(58) Field of Search ........................... 530/387.1, 387.3, 530/388.75, 388.8, 388.85, 300, 350; 424/130.1, 134.1, 181.1, 183.1; 512/2

(56) References Cited

U.S. PATENT DOCUMENTS

| | | | | |
|---|---|---|---|---|
| 4,359,457 | A | | 11/1982 | Neville, Jr. et al. |
| 4,440,747 | A | | 4/1984 | Neville, Jr. et al. |
| 4,500,637 | A | | 2/1985 | Neville, Jr. et al. |
| 4,520,011 | A | | 5/1985 | Neville, Jr. et al. |
| 4,520,226 | A | | 5/1985 | Neville, Jr. et al. |
| 5,747,654 | A | | 5/1998 | Pastan et al. |
| 5,762,927 | A | | 6/1998 | Knechtle et al. |
| 5,977,322 | A | * | 11/1999 | Marks et al. |

FOREIGN PATENT DOCUMENTS

| | | |
|---|---|---|
| WO | WO 98/39363 | 9/1998 |

OTHER PUBLICATIONS

Jost et al., "Mammalian Expression and Secretion of Functional Single–chain Fv Molecules," The Journal of Biological Chemistry 269 (42):26267–26273, 1994.

Vallera et al., "Therapy for Ongoing Graft–Versus–Host Disease Induced Across the Major or Minor Histocompatibility . . . Immunotoxin," Blood 86(11):4367–4375, 1995.

Vallera et al., "Anti–Graft–Versus–Host Disease Effect of $DT_{390}$–Anti–CD3sFv, a Single–Chain Fv Fusion . . . T–Cell Receptor," Blood 88:2342–2353, 1996.

Vallera et al., "Renal dysfunction accounts for the dose limiting toxicity of $DT_{390}$anti–CD3sFv, a potential new . . . immunotoxin," Protein Engineering 10(9):1071–1076, 1997.

* cited by examiner

*Primary Examiner*—Sheela Huff
*Assistant Examiner*—Larry R. Helms
(74) *Attorney, Agent, or Firm*—Fish & Richardson P.C.

(57) ABSTRACT

The invention features fusion protein monomers, multimeric immunotoxic proteins, nucleic acids encoding fusion protein monomers, vectors containing the nucleic acids, and cells containing the vectors. Also encompassed by the invention are methods of killing pathogenic cells and making multimeric immunotoxic proteins.

28 Claims, 9 Drawing Sheets

MULTIMERIC IMMUNOTOXINS

Some of the research described in this application was funded by a grant (R10-CA36725) from the National Institutes of Health. The U.S. government may therefore have certain rights in the invention.

BACKGROUND OF THE INVENTION

The invention is generally in the field of immunotoxins, particularly immunotoxins effective against pathogenic cells, e.g., T lymphocytes mediating graft-versus-host-disease (GVHD).

Immunotoxins are molecules that contain targeting domains that direct the molecules to target cells of interest (e.g., effector T lymphocytes) and toxic domains that kill the target cells. They are thus useful in pathological conditions such as GVHD, cancer, autoimmune diseases, and certain infectious diseases. The field of immunotoxins has been limited by an inability to escalate the dose of immunotoxin administered to a subject to a level that is therapeutic but not unacceptably toxic.

SUMMARY OF THE INVENTION

The invention derives from the finding that treatment of animals undergoing lethal GVHD with a homodimeric immunotoxin abrogated the GVHD. Treatment with this immunotoxin allowed for a therapeutic window in that the dose of the dimeric immunotoxin required for abrogation of GVHD was more than four-fold lower than the toxic dose. The invention includes monomeric fusion proteins useful for the production of multimeric immunotoxic proteins, multimeric immunotoxic proteins, nucleic acid molecules encoding fusion protein monomers, vectors containing the nucleic acid molecules, and cells containing the vectors. Also included in the invention are in vitro and in vivo methods of killing a target cell involving delivery of a multimeric immunotoxic protein to the surface of a target cell and methods of producing both a fusion protein monomer of the invention and the multimeric immunotoxic proteins of the invention.

More specifically, the invention features a fusion protein molecule containing a toxic domain, a targeting domain, and at least one heterologous coupling moiety. In this fusion protein, cysteine residues forming disulfide bonds are cysteine residues native to the toxic domain or the targeting domain. Other aspects of the invention are: (a) an isolated nucleic acid molecule containing a nucleic acid sequence encoding the above fusion protein; (b) a vector containing the nucleic acid molecule of (a), e.g., a vector in which transcriptional regulatory elements (TRE) are operably linked to the nucleic acid sequence; (c) a cell containing the vector of (b); and (d) a method of making a fusion protein in which the cell of (c) is cultured and the fusion protein is extracted from the culture, i.e., either from the culture medium or from the cells. The invention also provides a multimeric immunotoxic protein containing at least two of the above fusion protein molecules, each fusion protein molecule being joined by at least one of the heterologous coupling moieties to one or more of the other fusion protein molecules.

In addition, the invention encompasses a multimeric immunotoxic protein containing at least two fusion protein monomers, each of which includes a targeting domain and a toxic domain and is physically associated with the other fusion protein monomers. The targeting domain in all the multimeric immunotoxic proteins of the invention have significant binding affinity for a target molecule on a target cell. The fusion protein monomers can contain one or more coupling moieties and the physical association of the fusion protein monomer to one or more other fusion protein monomers can be mediated by at least one of the coupling moieties. The coupling moiety can be a terminal moiety, i.e., a C-terminal moiety or a N-terminal moiety. A coupling moiety can be, for example, a cysteine residue. Furthermore the coupling moieties can be heterologous coupling moieties. The fusion protein monomers in a particular multimeric immunotoxic protein can have the same amino acid sequence or different amino acid sequences. Targeting domains can be antibody fragments, e.g., single chain Fv and can have significant binding affinity for a target molecules on a T cell, e.g., a CD3 polypeptide. Alternatively, the targeting domain can be, for example, a polypeptide such as a cytokine, a ligand for a cell adhesion receptor, a ligand for a signal transduction receptor, a hormone, a molecule that binds to a death domain family molecule (e.g., Fas ligand, TNF-alpha, or TWEAK), an antigen, or a functional fragment of any of these polypeptides. The toxic domain can be, for example, any of the following toxic polypeptides: ricin, Pseudomonas exotoxin (PE), bryodin, gelonin, α-sarcin, aspergillin, restrictocin, angiogenin, saporin, abrin, pokeweed antiviral protein (PAP), or a functional fragment of any of these toxic polypeptides. The toxic domain can also be diphtheria toxin (DT) or a functional fragment thereof, e.g., a fragment containing amino acid residues 1–389 of DT. The target cell to which the multimeric immunotoxic proteins of the invention bind can be in a mammal. The mammal can be one suspected of having graft-versus-host disease (GVHD). A target cell to which the multimeric immunotoxic proteins bind can be a cancer cell, e.g., a neural tissue cancer cell, a melanoma cell, a breast cancer cell, a lung cancer cell, a gastrointestinal cancer cell, an ovarian cancer cell, a testicular cancer cell, a lung cancer cell, a prostate cancer cell, a cervical cancer cell, a bladder cancer cell, a vaginal cancer cell, a liver cancer cell, a renal cancer cell, a bone cancer cell, and a vascular tissue cancer cell.

The invention also features a method of killing a target cell in which the target cell is contacted with any of the multimeric proteins of the invention. The contacting can be in vitro or the target cell can be in a mammal. Where the target cell is in a mammal, the multimeric immunotoxic protein per se can administered to the mammal. Alternatively, one or more nucleic acids encoding at least two fusion protein monomers can be administered to the mammal. In addition, the multimeric immunotoxic proteins can be delivered to a target cell by an ex vivo methodology which can, for example, involve: (a) providing a recombinant cell which is the progeny of a cell from the mammal or from another mammal and has been transfected or transformed ex vivo with a vector containing one or more nucleic acid sequences, each nucleic acid sequence encoding a fusion protein monomer with a different amino acid sequence, such that the recombinant cell expresses the multimeric protein; and (b) administering the recombinant cell to the mammal.

Also within the invention is a method of making a multimeric immunotoxic protein. The method can involve the steps of: (a) providing one or more cells, each of the cells containing a nucleic acid sequence encoding a fusion protein monomer composed of a targeting domain and a toxic domain, each monomer having a different amino acid sequence, and the nucleic acid sequence being operably linked to a TRE; (b) separately culturing each of the one or more cells; (c) extracting the fusion protein monomer from each of the cultures (cells or medium); (d) mixing the fusion protein monomers; and (e) exposing the mixed fusion protein monomers to conditions which allow multimerization of the fusion protein monomers.

"Polypeptide" and "protein" are used interchangeably and mean any peptide-linked chain of amino acids, regardless of length or post-translational modification.

As used herein, "operably linked" means incorporated into a genetic construct so that expression control sequences effectively control expression of a coding sequence of interest.

As used herein, the term "antibody fragments" refers to antigen-binding fragments, e.g., Fab, $F(ab')_2$, Fv, and single chain Fv fragments. Also included are chimeric antibody fragments in which the regions involved in antigen binding (e.g., complementarity determining regions (CDR) 1, 2, and 3) are from an antibody produced in a first species (e.g., a mouse or a hamster) and the regions not involved in antigen binding (e.g., framework regions) are from an antibody produced in a second species (e.g., a human).

As used herein, a "functional fragment" of a toxic polypeptide for use as a toxic domain in the fusion proteins of the invention is a fragment of the toxic polypeptide shorter than the full-length, wild-type toxic polypeptide but which has at least 5% (e.g., 10%, 20%, 30%, 40%, 50%, 60%, 70%, 80%, 90%, 95%, 99%, 100%, or even more) of the toxic activity of the full-length, wild-type toxic polypeptide. In vitro and in vivo methods for comparing the relative toxic activity of two or more test compounds are known in the art.

As used herein, a "functional fragment" of a targeting polypeptide for use as a targeting domain in the fusion proteins of the invention is a fragment of the targeting polypeptide shorter than the full-length,wild-type targeting polypeptide but which has at least 5% (e.g., 10%, 20%, 30%, 40%, 50%, 60%, 70%, 80%, 90%, 95%, 99%, 100%, or even more) of the ability of the full-length, wild-type targeting polypeptide to bind to its relevant target molecule. Methods of comparing the relative ability of two or more test compounds to bind to a target molecule are well-known to artisans in the field, e.g., direct or competitive ELISA.

As used herein, a "coupling moiety" in a fusion protein of the invention is a molecule that can be, but is not necessarily, an amino acid (e.g., cysteine or lysine), and which is inserted either internally or at a terminus (C or N) of the fusion protein. Coupling moieties can be residues that are present in native polypeptides (or functional fragments thereof) used as targeting or toxic domains or they can be heterologous. Coupling moieties serve as sites for joining of one fusion protein to another.

As used herein, a "heterologous moiety" in a polypeptide is a moiety that does not occur in the wild-type form(s) of the polypeptide or functional fragment(s) thereof.

As used herein, "physically associated" fusion proteins are fusion proteins that are either: (a) directly joined to each other by, for example, a covalent bond or interactions such as hydrophobic interactions or ionic interactions; or (b) are indirectly linked to each other by one or more intervening fusion proteins, each linked in a sequential fashion by the above bond or interactions.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., abrogating GVHD in mammalian subjects, will be apparent from the following description, from the drawings and from the claims.

DESCRIPTION OF THE PREFERRED EMBODIMENTS

Figure 1:
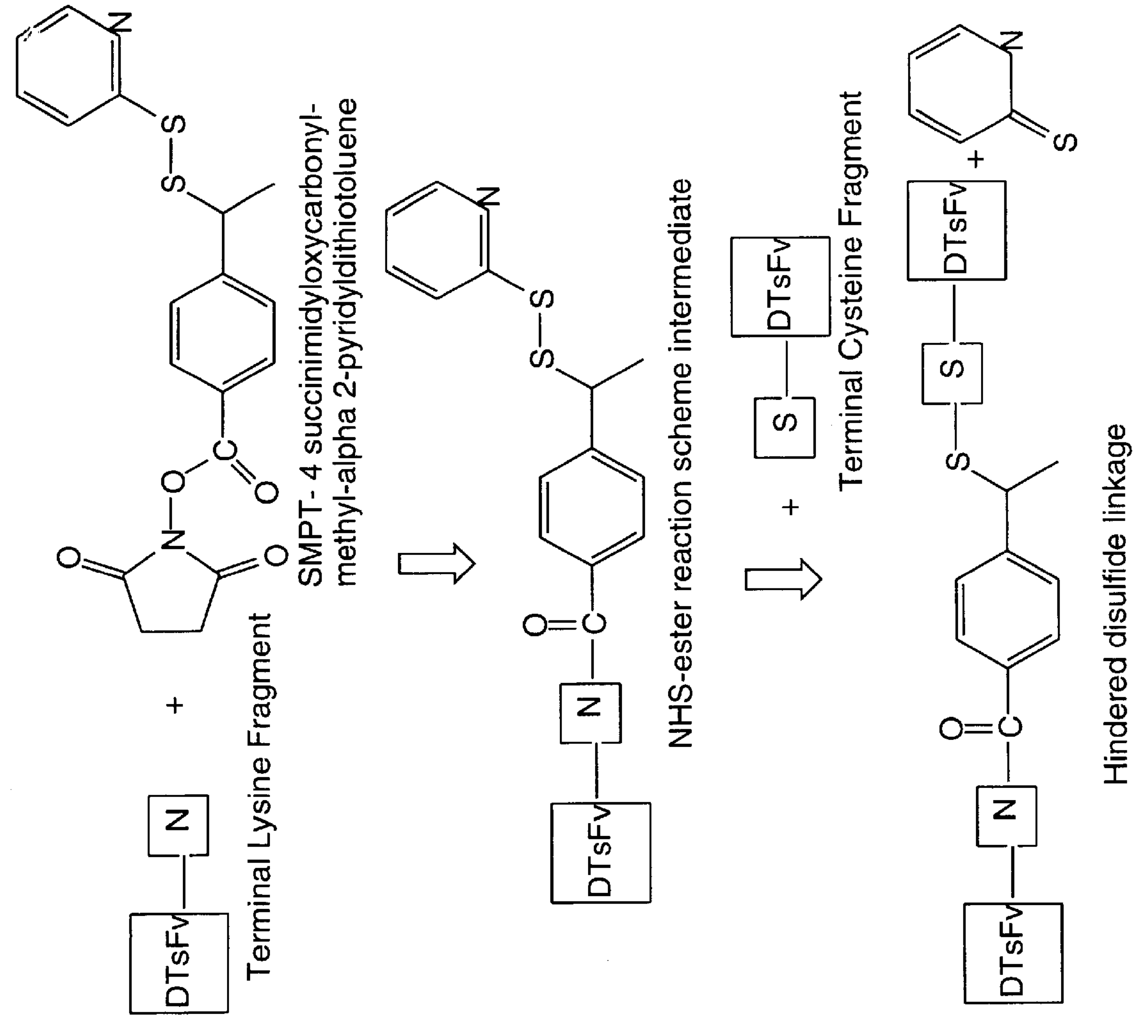
FIG. 1 is a depiction of the structure of SMPT and the structure of the hindered disulfide bond-containing linkage it forms between two polypeptides (designated DTsFv) containing a free sulfhydryl group (in a cysteine residue) and a free amino group (in a lysine residue).

The invention is based upon experiments with a homodimeric immunotoxin composed of two monomer polypeptides linked by a disulfide bridge formed through cysteine residues added recombinantly to the C termini of the monomer polypeptides. The monomer polypeptide contained: (a) a toxic domain (a portion of diphtheria toxin (DT)); (b) a targeting domain which was a single chain Fv fragment (sFv) derived from antibody specific for the $\epsilon$ chain of murine CD3, a molecular complex associated with the antigen-specific T cell receptor (TCR) and expressed on all T cells; and (c) a non-native cysteine residue added recombinantly to the C-terminus of the monomer polypeptide. The dimeric immunotoxin was shown to specifically target T cells in that T cells exposed, both in vitro and in vivo, to it had diminished proliferative responses while exposed B cells did not. In addition, the dimeric immunotoxin ablated lethal GVHD. Toxicity studies showed that, in the GVHD model, the therapeutic dose was at least four-fold lower than the toxic dose, thereby creating a "therapeutic window." In addition, the therapeutic dose had no effect on either renal or hepatic function.

A. Fusion Protein Monomers

The fusion protein monomers of the invention contain a targeting domain linked to a toxic domain, and a moiety by which one fusion protein monomer can be joined to another fusion protein monomer. Targeting and toxic domains are discussed in the following subsections and "coupling moieties" are described in the context of multimeric immunotoxins.

A.1 Targeting Domains

A targeting domain for use in the immunotoxins of the invention can be any polypeptide (or a functional fragment thereof) that has significant binding affinity for a target molecule on the surface of a target cell (e.g., a tumor cell or an infected cell). Thus, for example, where the molecule on the surface of the target cells is a receptor, the targeting domain will be a ligand for the receptor, and where the molecule on the surface of the target cells is a ligand, the targeting domain will be a receptor for the ligand. Targeting domains can also be functional fragments of appropriate polypeptides (see below).

The invention includes, as targeting domains, antibody fragments specific for a molecule on the surface of a target cell. Antibody fragments used as targeting domains in the immunotoxins of the invention contain the antigen combining site of an antibody molecule. The antibody fragments do not contain the whole constant region of either the heavy (H) or light (L) chain of an antibody molecule. However the antibody fragments can contain segments of the constant region of either or both the H and L chain. These constant region segments can be from the N-terminal end of the constant region or from any other part of the constant regions, e.g., the hinge region of IgG or IgA heavy chains. Where the antibody fragments contain constant region amino acid residues, they will contain not more than 20 (e.g., 19, 18, 17, 16, 15, 14, 13, 12, 11, 10, 9, 8, 7, 6, 5, 4, 3, 2, or 1) constant region amino acid residues.

An antibody fragment for use as a targeting domain contains V regions of both H and L chains of an antibody molecule. In addition, it can contain: (a) all or some of the J regions of both or either of the H and the L chain; and (b) the D region of the H chain. In general, the antibody will contain the CDR3 amino acid residues of an antibody molecule, i.e., those amino acids encoded by nucleotides at the C-termini of the V region gene segments, and/or P or N nucleotides inserted at the junctions of either the V and J, the V and D, or the D and J region gene segments during somatic B cell gene rearrangements necessary for the generation of functional genes encoding H and L chains. The antibody fragments can contain more than one (e.g., 2, 3, 4, or 5) antigen combining site, i.e., the above-described units containing components from both a H chain and a L chain.

Preferred antibody fragments are sFv fragments containing the V and, optimally, the CDR3 regions, of H and L chains joined by a flexible linker peptide. The term V region, as used in all subsequent text, unless otherwise stated, will be understood to include V regions alone and V regions and P/N nucleotides, and/or D regions, and/or J regions. They can also optionally contain up to 20 C region amino acids. Generally, but not necessarily, the heavy chain variable region (VH) will be C-terminal of the light chain variable region (VL). Linker peptides joining VH and VL regions can be 1 to about 30, even 50, amino acids long and can contain any amino acids. In general, a relatively large proportion (e.g., 20%, 40%, 60%, 80%, 90%, or 100%) of the amino acid residues in the linker will be glycine and/or serine residues.

Antibody fragments can be specific for (i.e., will have significant binding affinity for) a molecule expressed on the surface of a target cell of interest. Thus, the antibody fragments can have specific binding affinity for molecules such as T cell surface molecules (e.g., CD3 polypeptides, CD4, CD8, CD2, CD7, cytokine or growth factor receptors (see below), or TCR), B cell surface molecules a(e.g., CD19, CD20, CD22, cytokine or growth factor receptors, or Ig molecules), molecules expressed on tumor cells (e.g., those listed above for T and B cells, as well as others known in the art, e.g., melanoma, breast (e.g., her2/neu), ovarian, or colon cancer antigens), and molecules expressed on the surface of infected target cells (e.g., viral proteins and glycoproteins).

The targeting domains can also be immunoglobulin (Ig) molecules of irrelevant specificity (or immunoglobulin molecule fragments that include or contain only an Fc portion) that can bind to an Fc receptor (FcR) on the surface of a target cell (e.g., a tumor cell).

The targeting domains can be cytokines (e.g., IL-1, IL-2, IL-3, IL-4, IL-5, IL-6, IL-7, IL-8, IL-10, IL-12, IL-13, IL-15, the interferons (α, β, and γ), TNF-α, vascular endothelial growth factor (VEGF), and epidermal growth factor (EGF) colony stimulating factors (e.g., GM-CSF), hormones (e.g., insulin, or growth hormone), ligands for signal transduction receptors (e.g., CD40 ligand, an MHC class I molecule or fragments of an MHC molecule involved in binding to CD8, an MHC class II molecule or the fragment of an MHC class II molecule involved in binding to CD4), or ligands for adhesion receptors, e.g., ICAM-1, ICAM-2, or fibronectin or a domain (e.g., one containing one or more of the "Arg-Gly-Asp" repeats) of fibronectin involved in binding to integrin molecules. In addition a targeting domain could be Fas or Fas ligand or other death domain containing polypeptides (e.g., members of the TNF receptor family) or ligands for such polypeptides (e.g., TNF-α, or TWEAK)

In addition, in certain B cell lymphomas, the specificity of the cell surface Ig molecules has been defined. Thus, where such B cell lymphoma cells are the target cells, an immunotoxin of the invention could include, as the targeting domain, the antigen or a fragment containing the relevant antigenic determinant for which the surface Ig on the lymphoma cells is specific and thus has significant binding affinity. Such a strategy can also be used to kill B cells which are involved in the pathology of an autoimmune disease (e.g., systemic lupus erythematosus (SLE) or myasthenia gravis (MG)) and which express on their surface an Ig receptor specific for an autoantigen.

Similarly, malignant T cells or autoreactive T cells expressing a TCR of known specificity can be killed with an immunotoxin protein containing, as the targeting domain, a soluble MHC (class I or class II) molecule, an active (i.e., TCR-binding) fragment of such a molecule, or a multimer (e.g., a dimer, trimer, tetramer, pentamer, or hexamer) of either the MHC molecule or the active fragment. All these MHC or MHC-derived molecules can contain, within their antigenic peptide-binding clefts, an appropriate antigenic peptide. Appropriate peptide fragments could be from collagen (in the case of RA), insulin (in IDDM), or myelin basic protein (in MS). Tetramers of MHC class I molecules containing an HIV-1-derived or an influenza virus-derived peptide have been shown to bind to CD8+ T cells of the appropriate specificity [Altman et al. (1996), Science 274:94–96; Ogg et al. (1998), Science 279:2103–2106], and corresponding MHC class II multimers would be expected to be similarly useful with CD4+ T cells. Such complexes could be produced by chemical cross-linking of purified MHC class II molecules assembled in the presence of a peptide of interest or by modification of already established recombinant techniques for the production of MHC class II molecules containing a single defined peptide [Kazono et al. (1994), Nature 369:151–154; Gauthier et al. (1998), Proc. Natl. Acad. Sci. U.S.A. 95:11828–11833]. The MHC class II molecule monomers of such multimers can be native molecules composed of full-length α and β chains. Alternatively, they can be molecules containing either the extracellular domains of the α and β chains or the α and β chain domains that form the "walls" and "floor" of the peptide-binding cleft.

In addition, the targeting domain could be a polypeptide or functional fragment that binds to a molecule produced by or whose expression is induced by a microorganism infecting a target cell. Thus, for example, where the target cell is infected by HIV, the targeting domain could be an HIV envelope glycoprotein binding molecule such as CD4, CCR4, CCR5, or a functional fragment of any of these.

The invention also includes artificial targeting domains. Thus, for example, a targeting domain can contain one or more different polypeptides, or functional fragments thereof, that bind to a target cell of interest. Thus, for example, a given targeting domain could contain whole or subregions of both IL-2 and IL-4 molecules or both CD4 and CCR4 molecules. The subregions selected would be those involved in binding to the target cell of interest. Methods of identifying such "binding" subregions are known in the art. In addition, a particular binding domain can contain one or more (e.g., 2,3, 4, 6, 8, 10, 15, or 20) repeats of one or more (e.g., 2, 3, 4, 6, 8, 15, or 20) binding subregions of one or more (e.g., 2, 3, 4, or 6) polypeptides that bind to a target cell of interest.

The targeting domains can be polypeptides of any species, e.g., a human, non-human primate (e.g., monkey), mouse, rat, guinea pig, hamster, cow, sheep, goat, horse, pig, rabbit, dog, or cat.

The amino acid sequence of the targeting domains of the invention can be identical to the wild-type sequence of appropriate polypeptide. Alternatively, the targeting domain can contain deletions, additions, or substitutions. All that is required is that the targeting domain have at least 5% (e.g., 10%, 20%, 30%, 40%, 50%, 60%, 70%, 80%, 90%, 95%, 99%, 100%, or even more) of the ability of the wild-type polypeptide to bind to the target molecule. Substitutions will preferably be conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

Particularly useful as targeting domains are those whose nucleotide sequences have been defined and made public. Indeed, the nucleotide sequences encoding the H and L chains of many appropriate antibodies have been defined and are available to the public in, for example, scientific publications or data bases accessible to the public by mail or the internet. For example, the nucleic acid sequences (and references disclosing them) encoding the following polypeptides were obtained from GenBank at the National Center for Biotechnology Information, National Library of Medicine, Bethesda, Md.: VH and VL of an antibody specific for human CD4 [Weissenhorn et al. (1992) Gene 121(2):271–278]; VH and VL of an antibody specific for human CD3 [GenBank Accession Nos. AF078547 and AF078546]; VH and VL of an antibody specific for human CD7 [Heinrich et al. (1989) J. Immunol. 143:3589–3597]; human IL-1α [Gubler et al. (1986) J. Immunol. 136(7):2492–2497]; human IL-3 [Yang et al. (1986) Cell 47(1):3–10]; human IL-4 (genomic DNA sequence) [Arai et al. (1989) J. Immunol. 142(1):274–282]; human IL-4 (cDNA sequence) [Yokota et al. (1986) Proc. Natl. Acad. Sci. U.S.A. 83(16):5894–5898]; human GM-CSF [Wong et al. (1985) Science 228(4701):81–815]; human VEGF [Weindel et al. (1992) Biochem. Biophys. Res. Comm. 183(3):1167–1174]; human EGF [Bell et al. (1986) Nucleic Acids Res. 14(21):8427–8446]; and human CD40 ligand [Graf et al. (1992) Eur. J. Immunol. 22(12):3191–3194].

However, the invention is not limited to the use of targeting domains whose nucleotide sequences are currently available. Methods of cloning nucleic acid molecules encoding polypeptides and establishing their nucleotide sequences are known in the art [e.g., Maniatis et al., Molecular Cloning: A Laboratory Manual (Cold Spring Harbor Laboratory, N.Y., 1989) and Ausubel et al. Current Protocols in Molecular Biology (Green Publishing Associates and Wiley Interscience, N.Y., 1989)]

A.2 Toxic Domains

Toxic domains useful in the invention can be any toxic polypeptide that mediates a cytotoxic effect on a cell. Preferred toxic polypeptides include ribosome inactivating proteins, e.g., plant toxins such as an A chain toxin (e.g., ricin A chain), saporin, bryodin, gelonin, abrin, or pokeweed antiviral protein (PAP), fungal toxins such as α-sarcin, aspergillin, or restrictocin, bacterial toxins such as DT or Pseudomonas exotoxin A, or a ribonuclease such as placental ribonuclease or angiogenin. As with the targeting domains, the invention includes the use of functional fragments of any of the polypeptides. Furthermore, a particular toxic domain can include one or more (e.g., 2, 3, 4, or 6) of the toxins or functional fragments of the toxins. In addition, more than one functional fragment (e.g. 2, 3, 4, 6, 8, 10, 15, or 20) of one or more (e.g., 2, 3, 4, or 6) toxins can be included in the toxic domain. Where repeats are included, they can be immediately adjacent to each other, separated by one or more targeting fragments, or separated by a linker peptide as described above.

The amino acid sequence of the toxic domains of the invention can be identical to the wild-type sequence of appropriate polypeptide. Alternatively, the toxic domain can contain deletions, additions, or substitutions. All that is required is that the targeting domain have at least 5% (e.g., 10%, 20%, 30%, 40%, 50%, 60%, 70%, 80%, 90%, 95%, 99%, 100%, or even more) of the ability of the wild-type polypeptide to kill relevant target cells. It could be desirable, for example, to delete a region in a toxic polypeptide that mediates non-specific binding to cell surfaces. Substitutions will preferably be conservative substitutions (see above).

Particularly useful as toxic domains are those toxic polypeptides whose nucleotide sequences have been defined and made public. Indeed, the nucleotide sequences encoding many of the toxic polypeptides listed above have been defined and are available to the public. For example, the nucleic acid sequences (and references disclosing them) encoding the following toxic polypeptides were obtained from GenBank at the National Center for Biotechnology Information, National Library of Medicine, Bethesda, Md.: gelonin [Nolan et al. (1993) Gene 134(2):223–227]; saporin [Fordham-Skelton et al. (1991) Mol. Gen. Genet. 229(3);460–466]; ricin A-chain [Shire et al. (1990) Gene 93:183–188]; α-sarcin [Oka et al. (1990) Nucleic Acids Res.

18(7):1897; restrictocin [Lamy et al. (1991) Mol. Microbiol. 5(7):1811–1815]; and angiogenin [Kurachi et al. (1985) Biochemistry 24(20) :5494–5499].

However, the invention is not limited to the use of toxic domains whose nucleotide sequences are currently available. Methods of cloning nucleic sequences encoding known polypeptides and establishing their nucleotide sequences are known in the art. [Maniatis et al., supra, Ausubel et al., supra].

Toxic and targeting domains can be disposed in any convenient orientation with respect to each other in the fusion proteins of the invention. Thus, the toxic domain can be N-terminal of the targeting domain or vice versa. The two domains can be immediately adjacent to each or they can be separated by a linker (see above).

Smaller fusion proteins (less than 100 amino acids long) can be conveniently synthesized by standard chemical means. In addition, fusion proteins can be produced by standard in vitro recombinant DNA techniques and in vivo recombination/genetic recombination (e.g., transgenesis), using the nucleotide sequences encoding the appropriate polypeptides or peptides. The fusion proteins can also be made by a combination of chemical and recombinant methods.

Methods well known to those skilled in the art can be used to construct expression vectors containing relevant coding sequences and appropriate transcriptional/translational control signals. See, for example, the techniques described in Sambrook et al., Molecular Cloning: A Laboratory Manual (2nd Ed.) [Cold Spring Harbor Laboratory, N.Y., 1989], and Ausubel et al., Current Protocols in Molecular Biology, [Green Publishing Associates and Wiley Interscience, N.Y., 1989].

Expression systems that may be used for small or large scale production of the fusion proteins of the invention include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, Saccharomyces and Pichia) transformed with recombinant yeast expression vectors containing the nucleic acid molecules of the invention (see below); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing fusion protein nucleotide sequences; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal, transfected with a plasmid vector or infected with a viral vector.

Fusion proteins of the invention also include those described above, but modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety.

B. Multimeric Immunotoxins

The multimeric immunotoxins of the invention will contain two or more (e.g., three, four, five, six, or eight) of the monomeric fusion proteins described above. In a preferred embodiment, they will be dimeric. Each monomer can be identical, i.e., contain the same targeting and toxic domains and have the same amino acid sequence. Alternatively, they can be different. Thus, they can contain, for example, the same targeting domains but different toxic domains, different targeting domains but the same toxic domains, or different targeting domains and different toxic domains. Where different targeting domains are used, they will generally have significant binding affinity for either the same cell-surface molecule or for different molecules on the surface of the same cell.

The monomer fusion proteins of the invention can be linked to each by methods known in the art. For example, a terminal or internal cysteine residue on one monomer can be utilized to form a disulfide bond with a terminal or internal cysteine residue on another monomer.

Monomers can also be cross-linked using any of a number of known chemical cross linkers. Examples of such reagents are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. In FIG. 1 is shown how one such reagent, 4-succinimidyloxycarbonyl-α-methyl-α (2-pyridyldithio)toluene (SMPT), would form such a linkage between two monomers (designated "DTsFv") utilizing a terminal lysine on one of the monomers and a terminal cysteine on the other. Heterobifunctional reagents which cross-link by a different coupling moiety on each monomer polypeptide can be particularly useful in generating, for example, dimeric immunotoxins involving two different monomers. Thus, the coupling moiety on one monomer could be a cysteine residue and on the other a lysine residue. In this way, the resulting dimers will be heterodimers rather than either homodimers or a mixture of homodimers and heterodimers. Other useful cross-linkers, which are listed in the Pierce Products catalog (1999/2000), include, without limitation, reagents which link two amino groups (e.g., N-5-Azido-2-nitrobenzoyloxysuccinimide), two sulfhydryl groups (e.g., 1,4-Bis-maleimidobutane) an amino group and a sulfhydryl group (e.g., m-Maleimidobenzoyl-N-hydroxysuccinimide ester), an amino group and a carboxyl group (e.g., 4-[p-Azidosalicylamido]butylamine), and an amino group and a guanadium group that is present in the side chain of arginine (e.g., p-Azidophenyl glyoxal monohydrate).

While these cross-linking methods can involve residues ("coupling moieties") that are native to either of the domains of the monomers, they can also be used to cross-link non-native ("heterologous") residues incorporated into the polypeptide chains. While not necessarily the case, such residues will generally be amino acids (e.g., cysteine, lysine, arginine, or any N-terminal amino acid). Non-amino acid moieties include, without limitation, carbohydrates (e.g., on glycoproteins) in which, for example, vicinal diols are employed [Chamow et al. (1992) J. Biol. Chem. 267, 15916–15922]. The cross-linking agent 4-(4-N-maleimidophenyl)butyric acid hydrazide (MPBH), for example, can be used to cross-link a carbohydrate residue on one monomer and a sulfhydryl group on another. They can be added during, for example, chemical synthesis of a monomer or a part of the monomer. Alternatively, they can be added by standard recombinant nucleic acid techniques known in the art.

The coupling moieties can be positioned anywhere in the monomer fusion proteins, provided that the activity of the resulting immunotoxin multimer is not compromised. Thus, the linkage must not result in disruption of the structure of a targeting domain such that it can no longer bind to the cell-surface molecule for which it is specific. Furthermore, the linkage must not result in the disruption of the structure of the toxic domain such that it ablates the ability of the immunotoxin to kill its respective target cell. Using standard binding and toxicity assays known to those in the art, candidate multimeric immunotoxins employing linkages involving different residues on the monomers can be tested for their ability to bind and kill target cells of interest. Using molecular modeling techniques, it will frequently be possible to predict regions on a targeting domain or toxic domain that would be appropriate for the insertion of moieties by which inter-monomer linkages could be formed. Thus, for example, regions predicted to be on the exterior surface of a targeting domain, but unlikely to be involved in binding to a target molecule, could be useful regions in which to an insert an appropriate moiety in the targeting domain. Similarly, regions predicted to be on exterior surface of a toxic domain, but unlikely to be involved in the toxic activity, could be useful regions in which to an insert an appropriate moiety in the toxic domain.

The coupling moieties will preferably be at the termini (C or N) of the monomers. They can be, as indicated above, a cysteine residue on each monomer, or a cysteine on one and a lysine on the other. Where they are two cysteine residues, cross-linking can be effected by, for example, exposing the monomers to oxidizing conditions.

It can be desirable in some cases to eliminate, for example, one or more native cysteine residues in a monomer in order to restrict cross-linking to only non-native moieties inserted into the monomers. A potentially troublesome cysteine could, for example, be replaced by an alanine or a tyrosine residue. This can be done by, for example, standard recombinant techniques. Naturally, these replacements should not, compromize the activity of the resulting multimeric immunotoxin (see above).

It is understood that in immunotoxins containing more than two monomers, at least one of the monomers will have more than one cross-linking moiety. Such multimers can be constructed "sequentially", such that each monomer is joined to the next such that the terminal two monomers in the chain only have one residue involved in an inter-monomer bond while the "internal" monomers each have two moieties involved in inter-monomer bonds. Alternatively, one monomer could be linked to multiple (e.g., 2, 3, 4, or 5) other monomers. In these cases the first monomer would be required to contain multiple native and/or non-native cross-linkable moieties. A multimeric immunotoxin could also be formed by a combination of these two types of structure.

C. Nucleic Acids Encoding Fusion Proteins

The invention includes nucleic acids (e.g., cDNA, genomic DNA, synthetic DNA, or RNA) encoding any of the above fusion proteins of the invention. The nucleic acids can be double-stranded or single-stranded (i.e., a sense or an antisense strand). A RNA molecule can be produced by in vitro transcription. The nucleic acid molecules are not limited to coding sequences and can include some or all of the non-coding sequences that lie upstream or downstream of a particular coding sequence. The nucleic acids can have nucleotide sequences that are identical to those of nucleic acids encoding the wild-type targeting and toxic domains. Alternatively, they can contain codons other than wild-type codons but which, due to the degeneracy of the genetic code, encode toxic or targeting domains with amino acid sequences identical to relevant wild-type polypeptides. Furthermore, the nucleic acids can encode targeting or toxic domains with any of the above described deletions, additions, or substitutions.

Generally, the nucleic acids will include "hybrid genes," containing a first portion and a second portion. The first portion will encode a targeting domain and second portion will encode a toxic domain. Between the first and second portions can be codons encoding a linker (see above). Furthermore, where required, the nucleic acids can contain one or more codons encoding a heterologous (i.e., not existing in the wild-type polypeptide) coupling moiety, e.g., cysteine or lysine.

The coding sequences contain a leader sequence that encodes a hydrophobic signal peptide. The leader sequence is at the 5' end of the sequence encoding the fusion protein. The signal peptide is generally immediately N-terminal of the mature polypeptide (fusion protein) but can be separated from it by one or more (e.g., 2, 3, 4, 6, 8, 10, 15 or 20) amino acids, provided that the leader sequence is in frame with the nucleic acid sequence encoding the fusion protein. The signal peptide, which is generally cleaved from the fusion protein prior to secretion, directs fusion proteins into the lumen of an appropriate cell's endoplasmic reticulum (ER) during translation and the fusion proteins are then secreted, via secretory vesicles, into the environment of the cell. In this way, the producing cells remain viable since interaction of the toxin with the protein synthetic machinery in the cytosol of the cell is prevented by the membrane bilayers of the ER and secretory vesicles.

Useful leader peptides can be the native leader peptide of the relevant targeting domain (e.g., VH or VL) or a functional fragment of the native leader. Alternatively, the leader can be that of another exported polypeptide. For example, the signal peptide can have the amino acid sequence MAISGVPVLGFFIIAVLMSAQESWA (SEQ ID NO:1). In addition, the peptide sequence KDEL (SEQ ID NO:2) has been shown to act as a retention signal for the ER.

The invention also includes vectors containing the above nucleic acids. The vectors are preferably expression vectors. In the expression vectors of the invention, the nucleic acid sequence encoding a fusion protein of interest with an initiator methionine and, preferably, a signal sequence is "operably linked" to one or more transcriptional regulatory elements (TRE), e.g., a promoter or enhancer-promoter combination.

A promoter is a TRE composed of a region of a DNA molecule, typically within 100 nucleotide pairs upstream of the point at which transcription starts. Promoters are clustered around the initiation site for RNA polymerase II. Enhancers provide expression specificity in terms of time, location, and level. Unlike a promoter, an enhancer can function when located at variable distances from the transcription site, provided a promoter is present. An enhancer can also be located downstream of the transcription initiation site. The coding sequence in the expression vector is operatively linked to a transcription terminating region. To bring a coding sequence under the control of a promoter, it is necessary to position the translation initiation site of the translational reading frame of the peptide or polypeptide between one and about fifty nucleotides downstream (3') of the promoter. A list of promoters is provided in Table 1.

TABLE 1

PROMOTERS

| PROMOTER TYPE | PROMOTER ELEMENT | REFERENCES |
| --- | --- | --- |
| CONSTITUTIVE | β-actin | Liu et al., Mol. Cell Biol. 10:3432–40 (1990) |
| | tubulin | Angelichio et al., Nucleic Acids Res. 19:5037–43 (1991) |
| | CMV | see Invitrogen |
| | SV40 enhancer | see Pharmacia |
| | RSV-LTR | see Invitrogen |
| | Adenovirus enhancer | Inoue et al., Biochem Biophys Res Commun 173:1311–6 (1990) |
| TISSUE-SPECIFIC | | |
| LIVER | serum amyloid A | Li et al., Nucleic Acids Res 20:4765–72 (1992) |
| | phenylalanine hydroxylase | Wang et al., J Biol Chem 269:9137–46 (1994) |
| | IGFBP-1 | Babajko et al., PNAS 90:272–6 (1993) |
| | apolipoprotein B | Brooks et al., Mol Cell Biol 14:2243–56 (1994) |
| | albumin | Pinkert et al., Genes Dev 1:268–76 (1987) |
| | vitellogenin | Corthesy et al., Mol Endocrinol 5:159–69 (1991) |
| | angiotensinogen | Brasier et al., Embo J 9:3933–44 (1990) |
| | haptoglobin | Yang et al., Genomics 18:374–80 (1993) |
| | PEPCK | Short et al., Mol Cell Biol 12:1007–20 (1992) |
| | factor IX | Jallat et al., Embo J 9:3295–301 (1990) |
| | transferrin | Idzerda et al., Mol Cell Biol 9:5154–62 (1989) |
| | β-fibrinogen | Dalmon et al., Mol Cell Biol 13:1183–93 (1993) |
| | kininogen | Chen et al., Mol Cell Biol 13:6766–77 (1993) |
| | CRP | Toniatti et al., Mol Biol Med 7:199–212 (1990) |
| KIDNEY | renin | Fukamizu et al., Biochem Biophys Res Commun 199:183–90 (1994) |
| HEART | cardiac myosin light chain | Lee et al., J Biol Chem 267:15875–85 (1992) |
| | cardiac troponin C | Parmacek et al., Mol Cell Biol 12:1967–76 (1992) |
| | α-cardiac myosin heavy chain | Gulick et al., J Biol Chem 266:9180–5 (1991) |
| | MCK | Johnson et al., Mol Cell Biol 9:3393–9 (1989) |
| | troponin I | |
| | atrial natriuretic factor | Rockman et al., PNAS 88:8277–81 (1991) erratum 88(21):9907 |
| LUNG | pulmonary surfactant protein SP-C | Glasser et al., Am J Physiol L349–56 (1991) |
| PANCREAS/ISLET | insulin | Dandoy et al., Nucleic Acids Res 19:4925–30 (1991); and Selden et al., Nature 321:525–8 (1986) |
| | pancreatic amylase | Osborn et al., Mol Cell Biol 7:326–34 (1987) |
| BRAIN/GLIA | GFAP | Brenner et al., J Neurosci 1030–7 (1994) |
| | JCV | Henson et al., J Biol Chem 269:1046–50 (1994) |
| | MBP | Miskimins et al., Brain Res Dev Brain Res 65:217–21 (1992) |
| | serotonin 2 receptor | Ding et al., Brain Res Mol Brain Res 20:181–91 (1993) |
| | myelin PO | Monuki et al., Mech Dev 42:15–32 (1993) |
| | myelin proteolipid protein | Berndt et al. J Biol Chem 267:14730–7 (1992) |
| INDUCIBLE | | |
| A) IMMUNE SYSTEM/NATURAL | IL-2 | Thompson et al., Mol Cell Biol 12:1043–53 (1992) |
| | IL-4 | Todd et al., J Exp Med 177:1663–74 (1993) |
| | IL-6 | Libermann et al., Mol Cell Biol 10:2327–34 (1990); and Matsusaka et al., PNAS 90:10193–7 (1993) |
| | IL-8 | Matsusaka et al., PNAS 90:10193–7 (1993) |
| | IL-10 | Kim et al., J Immunol 148:3618–23 (1992) |
| | TNF-α | Drouet et al., J Immunol 147:1694–700 (1991) |
| | IL-1 | Shirakawa et al., Mol Cell Biol 13:1332–44 (1993) |
| | MIP-1 | Grove et al., Mol Cell Biol 13:5276–89 (1993) |
| | IFN-γ | Penix et al., J Exp Med 178:1483–96 (1993) |
| | VCAM-1 | Iademarco et al., J Biol Chem 267:16323–9 (1992) |
| | ICAM-1 | Voraberger et al., J Immunol 147:2777–86 (1991) |
| | ELAM-1 | Whelan et al., Nucleic Acids Res 19:2645–53 (1991) |
| | tissue factor | Mackman et al., J Exp Med 174:1517–26 (1991) |
| | IFN-β | Visvanathan et al., Embo J 8:1129–38 (1989) |
| | c-jun | Muegge et al., PNAS 90:7054–8 (1993) |
| | junB | Nakajima et al., Mol Cell Biol 13:3017–41 (1993) |
| | c-fos | Morgan et al., Cell Prolif 25:205–15 (1992) |

TABLE 1-continued

PROMOTERS

| PROMOTER TYPE | PROMOTER ELEMENT | REFERENCES |
|---|---|---|
| | iNOS | Xie et al., J Exp Med 177:1779–84 (1993) |
| | G-CSF | Shannon et al., Growth Factors 7:181–93 (1992) |
| | GM-CSF | Miyatake et al., Mol Cell Biol 11:5894–901 (1991) |
| B) IMMMNE SYSTEM/SYNTHETIC multiple copies of binding sites | NF-KB | Lenardo et al., Cell 58:227–9 (1989) |
| | NF-IL6 | Akira et al., Embo J 9:1897–906 (1990) |
| | IL6-response element | Wegenka et al., Mol Cell Biol 13:276–88 (1993) |
| | CRE | Brindle et al., Curr Opin Genet Dev 2:199–204 (1992) |
| | AP-1 | Auwerx et al., Oncogene 7:2271–80 (1992) |
| | p91/stat combinations of multiple NF-KB and NF-ILG or combinations with the other elements | Larner et al., Science 261:1730–3 (1993) |
| C) EXOGENOUS/NON-MAMMALIAN | IPTG inducible/lac repressor/operon system | see Stratagene LacSwitch ™, La Jolla, CA |
| | ecdysone-inducible promoter/ecdysone receptor | Burtis et al., Cell 61:85–99 (1990) |
| | Na-salicylate-inducible promoter PG/regulator nahR | Yen, J Bacteriol 173:5328–35 (1991) |
| | nalidixic acid inducible recA promoter | Rangwala et al., Biotechnology 9:477–9 (1993) |

Suitable expression vectors include, without limitation, plasmids and viral vectors such as herpes viruses, retroviruses, vaccinia viruses, attenuated vaccinia viruses, canary pox viruses, adenoviruses, adeno-associated viruses, lentiviruses and herpes viruses, among others.

The expression vectors of the invention containing the above described coding sequences have a variety of uses. They can be used, for example, to transfect or transduce either prokaryotic (e.g., bacteria) cells or eukaryotic cells (e.g., yeast, insect, or mammalian) cells. Such cells can then be used, for example, for large or small scale in vitro production of the relevant fusion protein by methods known in the art (see above). In essence, such methods involve culturing the cells under conditions which maximize production of the fusion proteins and isolating the fusion proteins from the cells or from the culture medium. The transduced/transfected cells can be used as targeting cells for delivery of the immunotoxic protein to a target cell by administration of the transduced/transfected cells to a subject harboring the target cell. Alternatively, the vector itself can be delivered to the subject.

The cells of the invention can, for example, be transduced with: (a) a single expression vector containing a nucleic acid sequence (e.g., a genomic DNA sequence, a cDNA sequence, or an RNA sequence) encoding one of the above fusion proteins of the invention; (b) two (or more) vectors, each containing a coding sequence encoding a different fusion protein; or (c) a single vector containing (two more) coding sequence, each encoding a different fusion protein, and each coding sequence being separately transcribed and/or translated. In cases (b) and (c), the fusion proteins encoded by the two (or more) coding regions are designed so that they associate post-translationally within the target cell by either covalent (e.g., disulfide) bonds or non-covalent (e.g., hydrophobic or ionic) interactions to form multimeric proteins of the invention.

D. Administration of a Multimeric Immunotoxic Protein

The multimeric immunotoxic proteins of the invention can be delivered to a cell population in vitro in order, for example, to deplete the population of cells expressing a cell surface molecule to which the targeting domain of an appropriate fusion protein binds. For example, the population of cells can be bone marrow cells from which it desired to remove T cells prior to use of the bone marrow cells for allogeneic or xenogeneic bone marrow transplantation. Alternatively, it may be desirable to deplete bone marrow cells of contaminating tumor cells prior to use of the bone marrow cells for bone marrow transplantation (autologous, allogeneic, or syngeneic) in a cancer patient. In such in vitro administrations, the cells to be depleted can be cultured with: (a) the isolated Age multimeric immunotoxic protein itself; (b) one or more expression vectors encoding one or more fusion proteins capable of associating to form a multimeric immunotoxic protein; or (c) cells transduced or transfected with one or more expression vectors encoding one or more fusion proteins which associate to form a multimeric immunotoxic protein. The mixture is cultured to allow for production of the immunotoxin (where the vector or genetically manipulated cells are added), binding of the immunotoxin to the target cells, and killing of the target cells.

Alternatively, a multimeric immunotoxic protein can be administered as a therapeutic agent to a subject in which it is desired to eliminate a cell population expressing a cell surface molecule to which the targeting domain of the fusion protein binds. Appropriate subjects include, without limitation, transplant (e.g., bone marrow, heart, kidney, liver, pancreas, lung) recipients, those with any of a variety of tumors (e.g., hematological cancers such as leukemias and lymphomas, neurological tumors such as astrocytomas or glioblastomas, melanoma, breast cancer, lung cancer, head and neck cancer, gastrointestinal tumors, genitourinary tumors, and ovarian tumors, bone tumors, vascular tissue tumors), those with any of a variety of autoimmune diseases (e.g., RA, IDDM, MS, MG, or SLE), or those with an infectious disease involving an intracellular microorganism (e.g., *Mycobacterium tuberculosis,* Salmonella, influenza virus, measles virus, hepatitis C virus, human immunodeficiency virus, and *Plasmodium falciparum*). In transplant recipients, the multimeric immunotoxic protein is delivered, for example, to T cells, thereby resulting in the death of a substantial number, if not all, of the T cells. In the case of a hematopoietic (e.g., bone marrow) cell transplant, the treatment can diminish or abrogate both host-versus-graft rejection and GVHD. Delivery of an appropriate multimeric immunotoxic protein to tumor cells can result in the death of a substantial number, if not all, of the tumor cells. In the case of infection, the multimeric immunotoxic protein is delivered to the infected cells, thereby resulting in the death of a substantial number of, in not all, the cells and thus a substantial decrease in the number of, if not total elimination of, the microorganisms. In autoimmune diseases, the multimeric immunotoxic protein can contain a targeting domain directed at the T cells (CD4+ and/or CD8+) and/or B cells capable of producing antibodies that are involved in the tissue destructive immune responses of the diseases.

Subjects receiving such treatment can be any mammal, e.g., a human (e.g., a human cancer patient), a non-human primate (e.g., a chimpanzee, a baboon, or a rhesus monkey), a horse, a pig, a sheep, a goat, a bovine animal (e.g., a cow or a bull), a dog, a cat, a rabbit, a rat, a hamster, a guinea pig, or a mouse.

The therapeutic methods of the invention fall into 2 basic classes, i.e., those using in vivo approaches and those using ex vivo approaches.

D. 1 In Vivo Approaches

In one in vivo approach, the multimeric immunotoxic protein itself is administered to the subject. Generally, the immunotoxins of the invention will be suspended in a pharmaceutically-acceptable carrier (e.g., physiological saline) and administered orally or by intravenous infusion, or injected subcutaneously, intramuscularly, intraperitoneally, intrarectally, intravaginally, intranasally, intragastrically, intratracheally, or intrapulmonarily. They are preferably delivered directly to an appropriate tissue, e.g., lymphoid tissue such as spleen, lymph nodes, or gut-associated lymphoid tissue in which an immune response (as, for example, in GVHD or an autoimmune disease) is occurring. The dosage required depends on the choice of the route of administration, the nature of the formulation, the nature of the patient's illness, the subject's size, weight, surface area, age, and sex, other drugs being administered, and the judgment of the attending physician. Suitable dosages are in the range of 0.01–100.0 $\mu$g/kg. Wide variations in the needed dosage are to be expected in view of the variety of multimeric immunotoxic proteins available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

In another in vivo approach, an expression vector containing one or more coding sequences encoding one or more fusion proteins of the invention, each coding sequence being separately transcribed, can be delivered to an appropriate cell of the subject. Alternatively, more than one expression vector, each containing a coding sequence encoding a different fusion protein, can be delivered to the appropriate cell. As the latter process would require that each expression vector be incorporated into a cell of interest, the approach using a single vector containing one or more coding sequences will be more efficient. The fusion proteins are designed such that, after translation, the fusion proteins will be multimerized by normal physiological mechanisms within the cell. Thus, for example, the fusion proteins can be linked by the formation of inter-fusion protein disulfide bonds or by non-covalent hydrophobic interactions between two or more fusion proteins.

Expression vectors and genetic constructs can be any of those described above. Expression vectors can be administered systemically to a subject. However, expression of the coding sequence will preferably be directed to a tissue or organ of the subject containing the target cells. For example, expression can be directed to a transplanted tissue or cell (e.g., a hematopoietic cell). An appropriate expression vector can, for example, be delivered directly to a tumor or, at the time of surgery, to tissues in the region of the body of the subject from which the tumor was surgically removed. Similarly, expression vectors can be delivered directly to the site of an infection or an autoimmune attack, e.g., joints in RA or the pancreas in IDDM.

It is not required that expression of the fusion protein be directed to the target cell itself. Indeed, expression will preferably not be by the target cell alone since, in this case, killing of the target cells by the multimeric immunotoxic proteins would result in the depletion of the source of the multimeric immunotoxic protein.

Delivery of the expression vectors can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1–10 $\mu$m in diameter can be used. The expression vector is encapsulated in these microparticles, which are taken up by macrophages and gradually biodegraded within the cell, thereby releasing the expression vector. Once released, the expression vector is expressed within the cell. A second type of microparticle is intended not to be taken up directly by cells, but rather to serve primarily as a slow-release reservoir of expression vector that is taken up by cells only upon release from the microparticle through biodegradation. These polymeric particles should therefore be large enough to preclude phagocytosis (i.e., larger than 5 $\mu$m and preferably larger than 20 $\mu$m). Microparticles useful for nucleic acid delivery, methods for making them, and methods of use are described in greater detail in U.S. Pat. No. 5,783,567, incorporated herein by reference in its entirety.

Another way to achieve uptake of vectors is through the use of liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73:479]. Alternatively, tissue specific targeting can be achieved by the use of tissue-specific TRE. A variety of tissue specific TRE and relevant references are listed in Table 1.

Expression vectors can be administered in a pharmaceutically acceptable carrier. Pharmaceutically acceptable carriers are biologically compatible vehicles suitable for administration to a mammalian subject such as, for example, a human patient, e.g., physiological saline. A therapeutically effective amount is an amount of the expression vector which is capable of producing a medically desirable result in a treated mammal, e.g., a human patient. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of an expression vector is from approximately $10^6$ to $10^{12}$ copies of the expression vector. This dose can be repeatedly administered, as needed. Routes of administration include, without limitation, intramuscular, intravenous, subcutaneous, intraperitoneal, intrarectal, intravaginal, intranasal, intragastric, intratracheal, or intrapulmonary routes. In addition, administration can be oral or transdermal, employing a penetrant such as a bile salt, a fusidic acid or another detergent. The injections can be single or multiple (e.g., 2-, 3-, 4-, 6-, 8-, or 10-fold).

D.2 Ex Vivo Approaches

An ex vivo strategy can involve transfecting or transducing targeting cells obtained from the subject with an expression vector containing one or more coding sequence encoding one or more fusion proteins. For the reasons given above, where the multimeric immunotoxic protein contains more than one species of fusion protein, it is preferred to use a single vector encoding each fusion protein. The transfected or transduced targeting cells are then returned to the subject, either at the site of the disease or systemically. Cells for use in these ex vivo methods can be any of a wide range of types including, without limitation, fibroblasts, bone marrow cells, macrophages, monocytes, dendritic cells, epithelial cells, endothelial cells, keratinocytes, or muscle cells which act as a source of the fusion protein for as long as they survive in the subject.

The ex vivo methods include the steps of harvesting cells from a subject, culturing the cells, transfecting or transducing them with one or more expression vectors, and maintaining the cells under conditions suitable for expression of the fusion protein(s). Expression vectors and genetic constructs can be any of those described above. These methods are known in the art of molecular biology. The transfection or transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced are optionally selected, for example, for expression of the coding sequence or of a drug resistance gene. The cells may then be lethally irradiated (if desired) and injected or implanted into the patient.

While it is preferred that the cells to be used for the ex vivo methods be autologous (i.e., obtained from the subject to which they are being administered following genetic manipulation), it is understood that they need not be autologous.

These methods of the invention can be applied to any of the diseases and species listed here. Methods to test whether a multimeric immunotoxic protein is therapeutic for a particular disease can be by methods known in the art. Where a therapeutic effect is being tested, a test population of subjects displaying signs or symptoms of the disease (e.g., cancer or RA patients or experimental animals) is treated with a test multimeric immunotoxic protein, using any of the above described strategies. A control population, also displaying signs or symptoms of the disease, is treated, using the same methodology, with a placebo. Disappearance or a decrease of the disease signs or symptoms in the test subject indicates that the multimeric immunotoxic protein is an effective therapeutic agent.

The following examples are meant to illustrate, not limit, the invention.

EXAMPLES

Example 1

Materials and Methods

Figure 2:
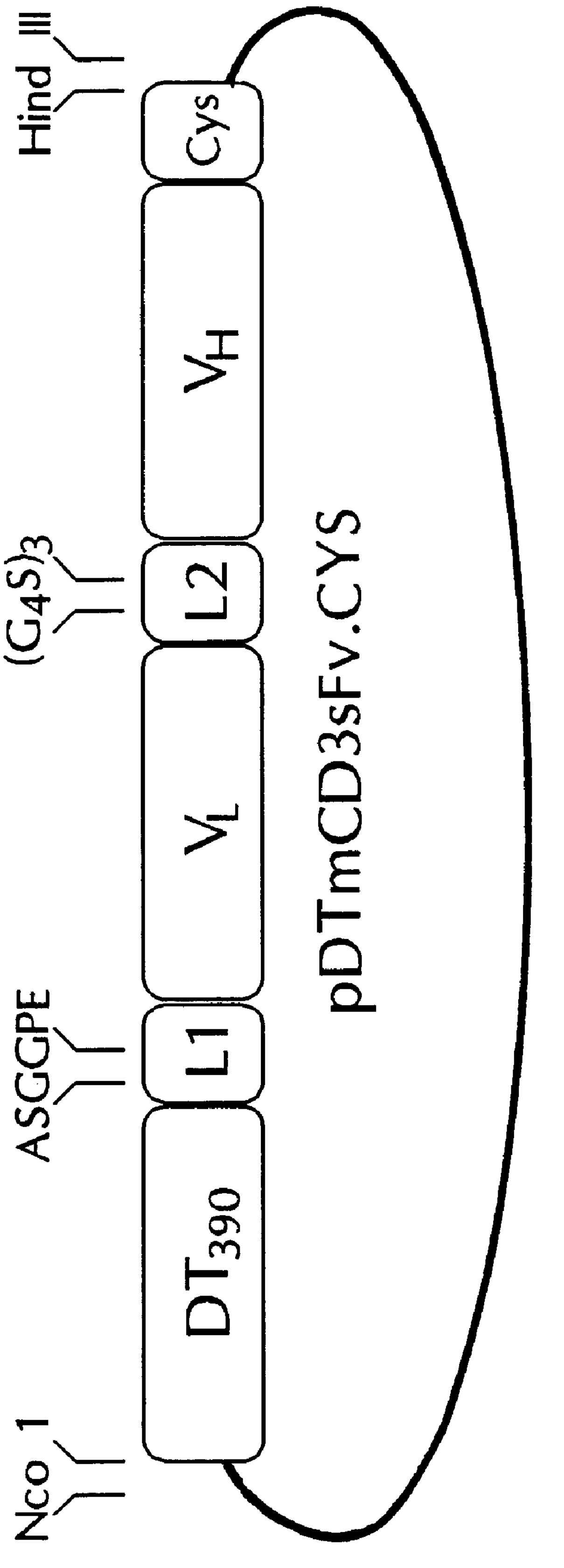
FIG. 2 is a depiction of the pDTmCD3sFv.Cys plasmid.

Construction of an expression vector. A 1.9 kb hybrid gene encoding an ATG initiation codon, the first 389 amino acids of diphtheria toxin (DT), a five amino acid residue (ASGGP) (SEQ ID NO:3) linker, and a sFv gene derived from hybridoma 145-2C11 (producing antibody specific for murine CD3) [Jost et al. (1994) J. Biol. Chem. 269:26267] was constructed using the method of gene splicing by overlap extension. In this sFv the light chain variable region ($V_L$) is separated from the heavy chain variable region ($V_H$) by a linker with the following amino acid sequence: GGGGSGGGGSGGGGS (SEQ ID NO:4) (("$G_4S)_3$"). The gene was cloned into the pET21d bacterial expression vector (InVitrogen) to create the plasmid pDTmCD3sFv. The plasmid was mutated by PCR using a forward primer 5'AGATATTCCATGGGCGCTGATGATGTTGTTGAT3' (SEQ ID NO:5) to introduce an NcoI site and a back primer 3'AAGCTTTTACTAACAGGAGACGGT5' (SEQ ID NO:6) to introduce C-terminal cysteine. DNA sequencing analysis verified that the coding sequences and mutations had been inserted in frame. The 1914 bp Nco1/HindIII fragment hybrid gene encoding the fusion protein ($DT_{390}$anti-CD3.cys) was spliced into the pET21d expression vector under the control of the isopropylthiogalactoside inducible T7 promoter creating plasmid pDTmCD3.cys (FIG. 2).

Expression of the fusion protein and generation of the dimeric immunotoxin.

Plasmid pDTmCD3.cys was transformed into *E. coli* strain BL21(DE3) bacteria (Novagen, Madison, Wis.) and protein expression was evaluated. Briefly, recombinant bacteria were grown in 4 L Superbroth supplemented with 100 ug/ml carbenicillin (Sigma, St. Louis, Mo.), at 37° C. When the absorbance ($A_{600}$) of culture reached 1.0, expression of the hybrid gene was induced by the addition of 1 mM isopropyl-β-D-thiogalactopyranoside (IPTG) (Gibco BRL, Gaithersburg, Md.). Ninety minutes after induction, the bacteria were harvested by centrifugation at 5000 g for 10 min, at 4° C.

To isolate expressed protein from inclusion bodies, the bacterial pellet was resuspended in TE buffer (50 mM Tris, pH 8.0, 20 mM EDTA, 100 mM NaCl) and treated with 5 mg/ml lysozyme for 1 hr. The pellet was then incubated in Triton X-100 buffer (11% v/v Triton X-100, 89% v/v TE) for 30 min at room temperature after briefly homogenizing with a tissuemizer (IKA LABORTECHNIK, Germany). Inclusion bodies were collected by centrifugation at 24,000 g for 50 min. The inclusion bodies were homogenized in the Triton X-100 buffer and centrifuged (as described above) an additional three times. Following the Triton X-100 washes, the inclusion bodies were homogenized in TE without Triton-X and centrifuged. This process was repeated four times.

Solubilization by sonication and reduction of the fusion protein to generate the dimeric immunotoxin was achieved in a buffer consisting of 7 M guanidine, 0.1M Tris, pH 8.0, 2 mM EDTA, and 65 mM dithioerythreitol (DTE). The solution was incubated at room temperature for 16 hr. To remove insoluble material, the solution was centrifuged at 40,000 g for 10 min at room temperature. Protein concentrations were determined according to the Bradford method [Bradford M. M. (1976) Anal. Biochem. 72:248]. To ensure proper tertiary structure, renaturation was initiated by a rapid 100-fold dilution of the denatured and reduced protein into refolding buffer consisting of 0.1M Tris, pH 8.0, 0.5 M L-arginine, 0.9 mM oxidized glutathione (GSSG), and 2 mM EDTA. The samples were incubated at 10° C. for 48 hr. The refolded protein was diluted ten-fold in distilled water and loaded on a Q-Sepharose (Sigma, St. Louis, Mo.) column and eluted with 0.2 M NaCl in 20 mM Tris, pH 7.8. The eluant was concentrated and dialyzed against PBS, pH 7.5. The main peak was purified by size-exclusion chromatography on a TSK GS3000SW column (TosoHass, Philadelphia, Pa.). Two fractions were collected that were enriched for the monomeric and dimeric forms of the immunotoxin. The fraction enriched for dimeric $DT_{390}$anti-CD3.cys protein was called SS2.

Purified fusion proteins were analyzed using 10% SDS-PAGE gels (Bio-Rad, Richmond, Calif.) and a Mini-Protean II gel apparatus (Bio-Rad, Richmond, Calif.). Proteins were stained with Coomassie brilliant blue.

Monoclonal antibodies and biochemical immunotoxins. Monoclonal antibodies included: 145–2C11, a hamster IgG reactive with the ε-chain of the murine CD3 complex [Leo et al. (1984) Proc. Natl. Acad. Sci. USA 1087:1374]: the anti-CD3 antibody was used in the blocking studies. A rat IgG2a monoclonal antibody specific for murine Ly5.2 (from clone A20-1.7) was used as a control since it recognized a hematopoietic cell surface marker not expressed in the mice used in these studies.

Mitogen bioassays. To measure mitogen induced cell proliferation, single cell suspensions of C57BL/6 splenocytes were prepared in Dulbecco's Modified Eagle's Medium (DMEM) [Vallera et al. (1996) Blood 88:2342]. Red blood cells were lysed using ACK lysis buffer. Cells ($10^5$) were plated in the wells of 96-well flat-bottom tissue culture plates in DMEM supplemented with 10% fetal bovine serum, 2-mercaptoethanol (100 uM), various concentrations of immunotoxin, and PHA (12 ug/ml) PHA (Sigma, St. Louis, Mo.) or Concanavalin A (ConA) (10 ug/ml) (Sigma) to induce T cell proliferation. To measure B cell proliferation, cultures were similarly prepared, but stimulated with 50 ug/ml lipopolysaccharide (LPS) (Difco Laboratories, Detroit, Mich.). The plates were incubated at 37° C., 10% $CO_2$ for 48 hr, all wells were pulsed with 1 uCi [$^3$H]-thymidine and the plates were incubated at 37° C., 10% $CO_2$, for a further 24 hours. Cells were harvested onto glass fiber filters, washed, dried and counted using standard scintillation counting methods.

In vitro viability assays. The 2B4 cell line is a T cell hybridoma expressing an antigen-specific T cell receptor and the associated CD3 complex [Samelson et al. (1983) Proc. Natl. Acad. Sci. USA 80, 6972]. Two hundred thousand 2B4 cells were plated into individual wells of a 24-well flat-bottom tissue culture plate (Costar, Cambridge, Mass.) in RPMI 1640 tissue culture medium containing 10% fetal bovine serum (Hyclone, Logan, Utah) in the presence of varying concentrations of SS2. Assays were performed in triplicate. At 24, 48, and 72 hr a small sample was removed from each well and stained with trypan blue dye to quantitate the number of cells in the wells and their viability.

Flow Cytometry. Flow cytometry was used to analyze the effect of the IT on T cell subpopulations. The following mAb were used: anti-CD4 (clone GK 1.5 provided by Dr Frank Fitch, University of Chicago, Chicago, Ill.) [Dialynas et al. (1983) J. Immunol. 131:2445], anti-CD8 (clone 53–6.72, rat IgG2a provided by Dr Jeffrey Ledbetter, Bristol-Myers-Squibb, Seattle, Wash.) [Ledbetter et al. (1980) J. Exp. Med. 152:280], anti-T cell receptor α/β [Kubo et al. (1989) J. Immunol. 142:2736], and an irrelevant rat $IgG_2$ antibody (3A1E) [Jansen et al. (1992) Cancer Res. 52:1314] (used as a negative control). Monoclonal antibodies were purified [Ey et al. (1978) Immunochem. 15:429] and directly labeled with fluorescein isothiocyanate (FITC) and phycoerythrin (PE) as described [Blazar et al. (1991) J. Immunol. 147:1492]. Two-color cytometry studies were performed on single cell suspensions of lymph nodes, spleens and thymi from toxin treated mice. The cells were washed and resuspended in FACS buffer (PBS supplemented with 2.5% newborn calf serum and 0.01% sodium azide). One million pelleted cells were incubated for 10 min at 40° C. with 0.4 ug of an anti-Fc receptor mAb [Unkless J.C. (1979) J. Exp. Med. 150:580] to prevent Fc binding. Optimal concentrations of PE- and FITC-labeled mAb were added to a total volume of 100 ul and incubated 1 hr at 4° C. Cells were washed three times with FACS buffer and after the final washing were fixed in 1% formaldehyde. All samples were analyzed on a FACscan (Becton Dickinson, Palo Alto, Calif.) using Consort-30 software. A minimum of 20,000 events was examined. Background subtraction using directly conjugated irrelevant antibody control was performed for each sample.

Mice. C57BL/6 ($H2^b$) mice (abbreviated B6) were purchased from NIH (Bethesda, Md.). B6 congenic mice containing a mutation in a MHC class II H-2 IA gene (B6.C-$H2^{bm12}$) (abbreviated bm12) were purchased from the Jackson Laboratory (Bar Harbor, Me.). For bone marrow transplants, donors were 4–6 weeks of age and recipients were 8–10 weeks of age at the time of BMT. All mice were housed in a specific pathogen-free facility in microisolator cages.

GVHD Model. To induce lethal GVHD, bm12 recipients were irradiated sublethally (6.0 Gy total body irradiation from a $^{137}$Cs source at a dose rate of 85 cGy/min), and injected with enriched lymph node T cells as previously described [Blazar et al. (1997) Transplantation 64:571]. To prepare lymph node (LN) cells, single-cell suspensions of axillary, mesenteric, and inguinal LIN cells were obtained (as a source of GVHD-causing effector cells) by passing minced LN through a wire mesh and collecting them into RPMI 1640 tissue culture medium. Cell preparations were depleted of B cells by passage through a goat anti-mouse immunoglobulin-coated column (Biotex, Edmonton, Canada). One million T cell-enriched C57BL/6 lymph node cells were administered via caudal vein in 0.5 ml. The development of GVHD was assessed by survival and weight loss.

Pathologic Examination of Tissues. Mice were sacrificed, autopsied, and tissues were taken for histopathologic analysis as described [Blazar et al. (1996) Blood 87:827]. All samples were embedded in OCT compound (Miles, Elkhark, Ind.), snap frozen in liquid nitrogen, and stored at −80° C. until sectioned. To ensure maximum quality of frozen specimens, the whole process of sacrifice through freezing was performed in under 10 minutes for each mouse. Serial 4 $\mu$ sections were cut, thaw mounted onto glass slides and fixed for 5 min in acetone. Slides were stained with hematoxylin and eosin (H and E) for histopathologic analysis.

Immunohistochemistry. Frozen tissues (spleen and liver) were sectioned and stained with H and E. Sections were also immunohistochemically stained to detect expression of cell surface antigens. After blocking with 10% normal horse serum, sections were incubated with biotinylated mAb (purchased from PharMingen) specific for CD4 (GK1.5), CD8 (53-6.7), CD19 (1D3), or Mac-1+ macrophages/neutrophils (M1/70). Detection with alkaline phosphatase-conjugated avidin-biotin complex and BCIP/NBT as chromogen was performed essentially as described [Hsu et al. (1981) J. Histochem. and Cytochem. 29:577] with reagents purchased from Vector Laboratories, Inc. (Burlingame, Calif.).

Blood Urea Nitrogen (BUN) and alanine transferase (ALT) assays. As previously described [Vallera et al. (1997) Protein Eng. 10:1071], BUN and ALT assays were performed on Kodak EKTACHEM clinical chemistry slides on a Kodak ETACHEM 950 by the Clinical Chemistry Laboratory, Fairview University Medical Center-University Campus (Minneapolis, Minn.). Mice were sacrificed, and individual serum samples collected. Analyses were performed blindly on undiluted samples. Minimum specimen volume was 11 ul for each assay. The BUN assay is read spectrophotometrically at 670 nm. In the ALT assay, the oxidation of NADH is used to measure ALT activity at 340 nm.

Fusion toxin administration. Immunotoxins were given intraperitoneally (i.p.) in a 0.2 ml volume in the morning and then again 6–8 hr later. Doses recited are total daily doses administered bi-daily (BID).

Radiolabeling of SS2 and fusion protein monomer and biodistribution. SS2 and monomer were radiolabeled with $^{125}$I using the ATE method of Zalutsky and Narula [Zalutsky et al. (1987) Appl. Radiat. Isot. 38:1051]. Briefly, Na$^{125}$I (2.0 mCi) (DuPont/NEN Research Products, Boston, Mass.) was oxidized with t-butylhydroperoxide (4.5 mg) and incubated with 50 $\mu$g of N-succinimidyl-3-(tri-n-butylstannyl) benzoate (ATE) in 125 $\mu$l chloroform for 1 h at room temperature. The reaction mixture was purified by reversed-phase HPLC and concentrated to dryness. SS2 or monomer (110 $\mu$g) were added to the dried material (200 $\mu$Ci) and incubated at room temperature for 1 h. The reaction mixtures were purified using a PD-10 column (Pharmacia, Uppsala, Sweden) to yield $^{125}$I-mIP-SS2 at a specific activity of 0.8 $\mu$Ci/$\mu$g and $^{125}$I-mIP-monomer at a specific activity of 1.0 $\mu$Ci/$\mu$g. The radiolabeled products were analyzed by SDS-PAGE which demonstrated the same protein bands observed with unlabeled SS2 and monomer. Autoradiography of the gel showed that the radioactivity was associated with the protein bands. The $^{125}$I-mIP-SS2 and 125I-mIP-monomer were active as demonstrated by their specific binding to 2B4 cells and their cytotoxicity against EL4 cells. The $^{125}$I-mIP-SS2 and $^{125}$I-mIP-monomer were then evaluated for biodistribution in normal C57BL/6 mice (National Cancer Institute Frederick Research Laboratory, Frederick, Md.). Two $\mu$Ci of $^{125}$I-mIP-SS2 or $^{125}$I-mIP-monomer were injected i. v. into the mice which were sacrificed 30 minutes later. The kidney, liver, and heart were removed, weighed and the radioactivity counted in a gamma counter (Packard Auto Gamma 5000 Series, Chicago, Ill.). The percent of injected dose per gram for each tissue was calculated.

Statistical analyses. Groupwise comparisons of continuous data were made by Student's t-test. Survival data were analyzed by Mantel-Peto-Cox summary of chi square [Mantel, N. (1966) Cancer Chemotherapy 50:163]. Probability (p) values $\leqq 0.05$ were considered significant.

Example 2

Purity of the SS2 Fraction

Figure 3:
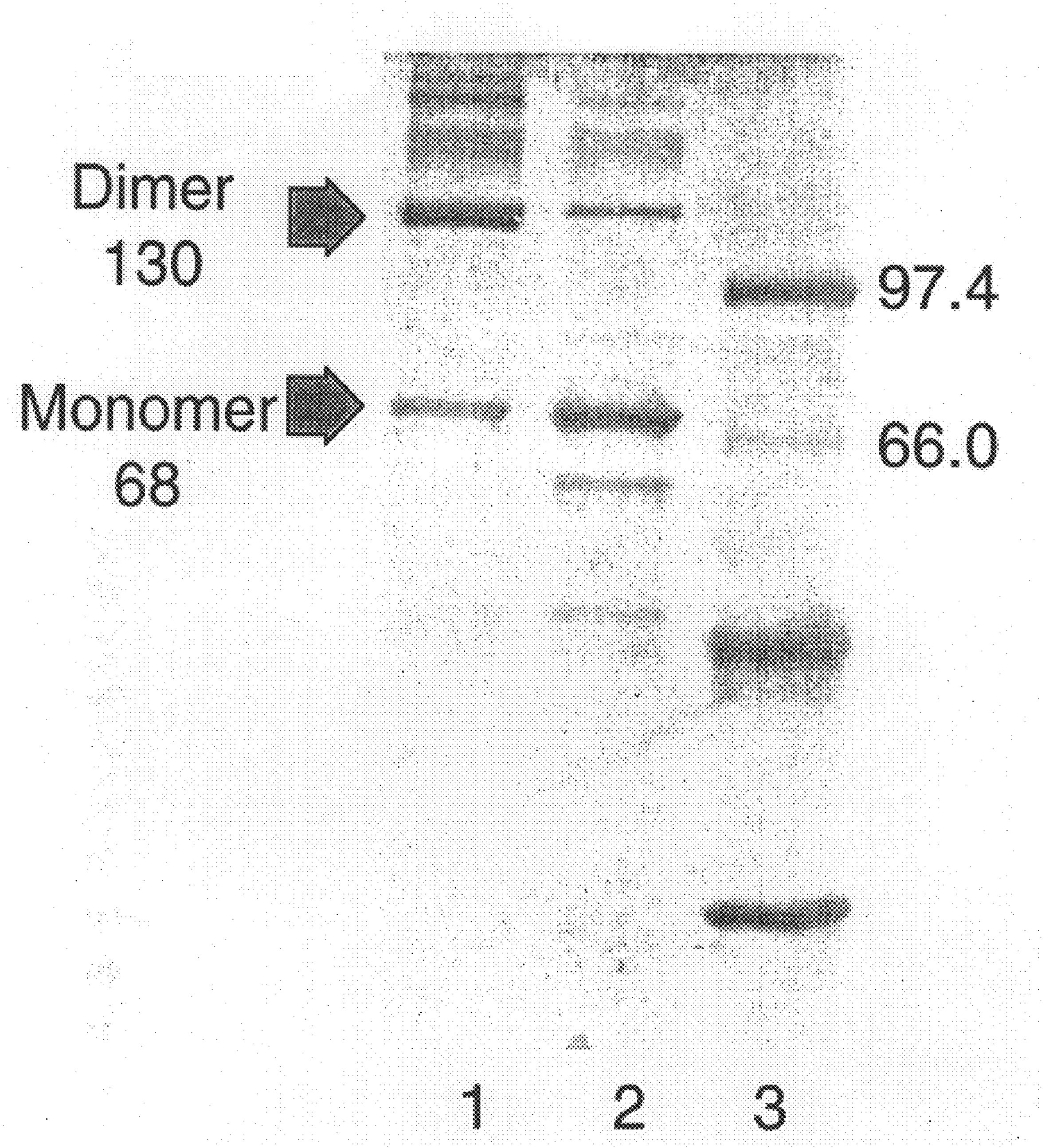
FIG. 3 is a photograph of a Coomassie blue stained SDS-PAGE gel showing the purity of the SS2 (lane 1) and monomeric immunotoxin enriched (lane 2) HPLC fractions. Lane 3 contains molecular weight standards.

To assess the purity of fractions collected from the chromatographic purification of the dimeric immunotoxin, SDS-PAGE analysis was performed (FIG. 3). The isoelectric point of the dimeric immunotoxin (i.e., a dimer of $DT_{390}$anti-CD3.cys) was 5.64 as determined using ISO-ELECTRIC (Genetics Computer Group, Wisconsin Package version 10.0-UNIX, Madison, Wis.). FIG. 3, lane 1 shows that the SS2 fraction consisted of about 74% dimer and about 26% monomer. Lane 2 shows that the monomeric fraction contained about 63% monomers, 20% dimer, and the remainder of the fraction was low molecular weight contaminants. Lane 3 shows molecular weight standards with the upper 2 bands representing 66 and 97.4 kDa.

Example 3

Figure 4A:
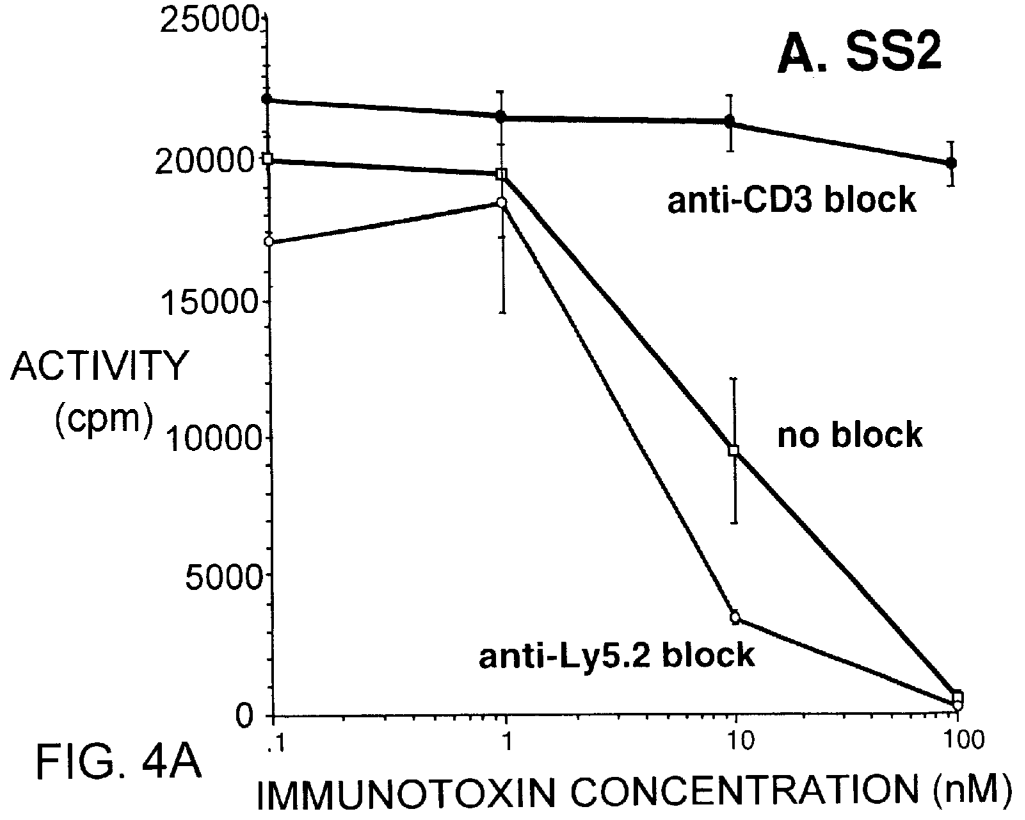
FIGS. 4A and 4B are line graphs showing the effect of the SS2 fraction (FIG. 4A) and monomeric immunotoxin (FIG. 4B) on in vitro PHA-induced T cell proliferation in cultures containing no inhibitor, anti-CD3 antibody, or irrelevant anti-Ly5.2 antibody.
Figure 4B:
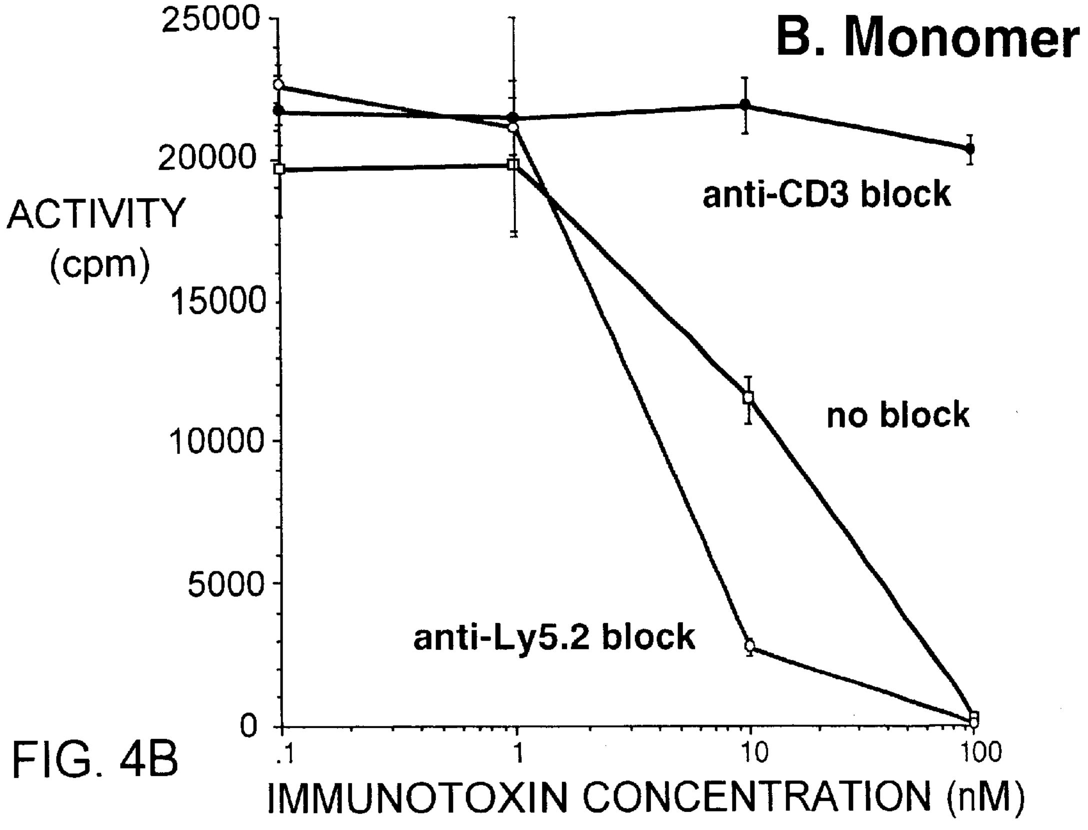

In vitro Activity of SS2 Measured Against Mitogen Stimulated T Cells and a T Cell Line To measure the activity and selectivity of SS2 against T cells, 2 different mitogenic assays were used. In the first assay, murine splenocytes were activated with the T cell mitogen PHA. FIG. 4A shows that T cell proliferation was inhibited in a dose dependent manner by SS2. The $IC_{50}$ (the concentration at which 50% of activity is inhibited) was about 10 nM SS2. Inhibition was selective since the addition of the parental 1452C11 anti-CD3 mAb, with specificity identical to that of the immunotoxin, entirely blocked IT activity. The addition of control anti-Ly5.2 mAb (which was not reactive with either SS2 or the splenocytes) had no blocking effect indicating that binding of the SS2 molecule was mediated entirely through the sFv moiety of the engineered protein. FIG. 4B indicates that the monomer had almost identical activity.

Figure 5A:
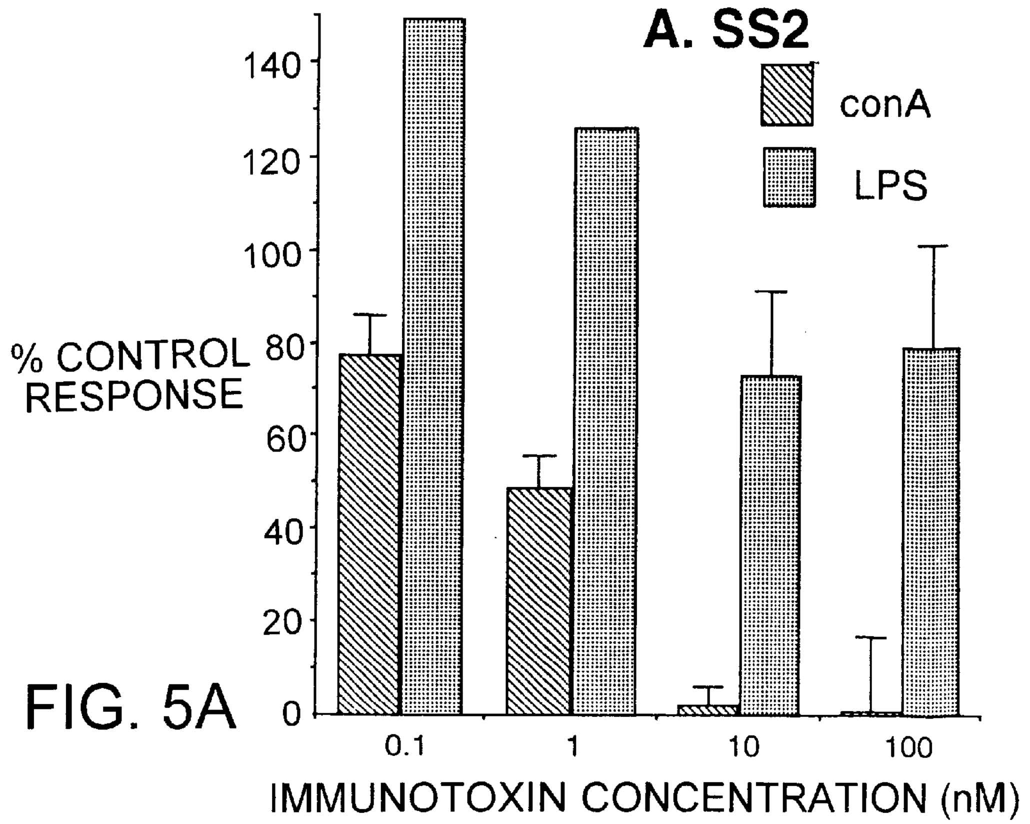
FIGS. 5A and 5B are bar graphs showing the effect of the SS2 fraction (FIG. 5A) and monomeric immunotoxin (FIG. 5B) on in vitro ConA-induced T cell proliferation and in vitro LPS-induced B cell proliferation.
Figure 5B:
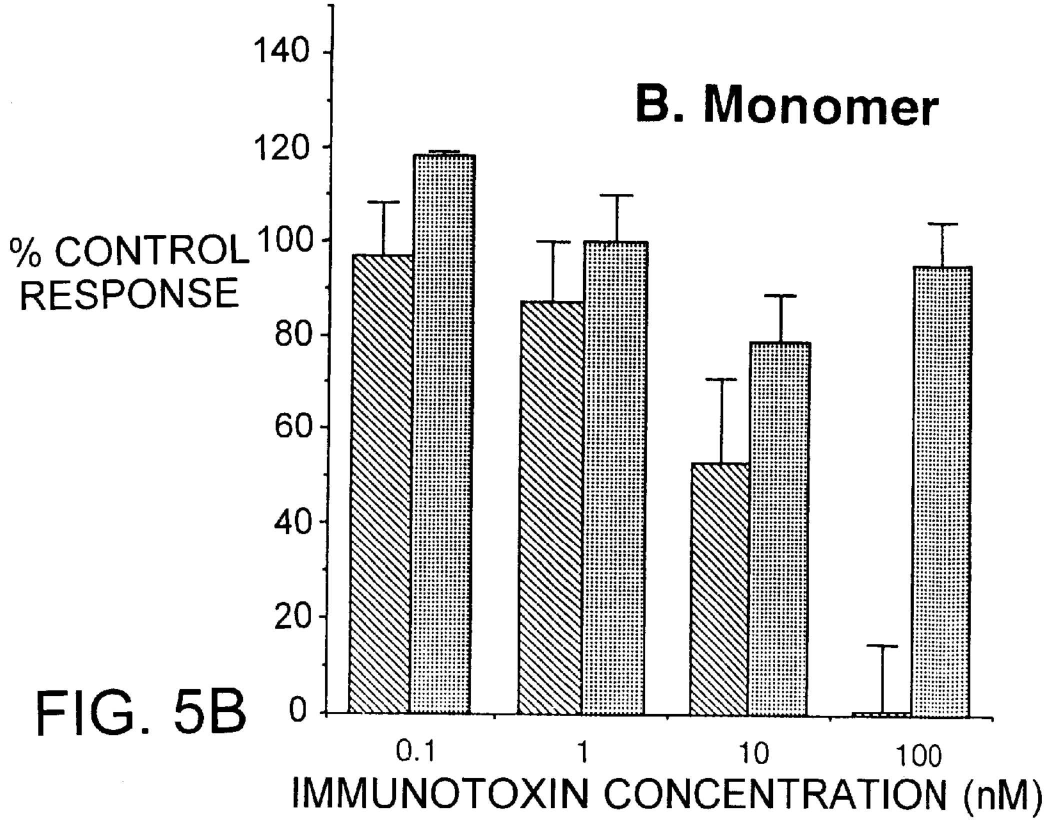

In a separate experiment, splenocytes were stimulated with ConA. FIG. 5A shows that 10 nM SS2 inhibited T cell proliferation by greater than 95%. In contrast, B cell proliferation measured by stimulating splenocytes with the B cell mitogen LPS, was minimally affected by SS2, even at a dose of 100 nM. FIG. 5B shows that a similar pattern of activity was observed for monomer. However, in this assay, SS2 was slightly more effective.

Figure 6A:
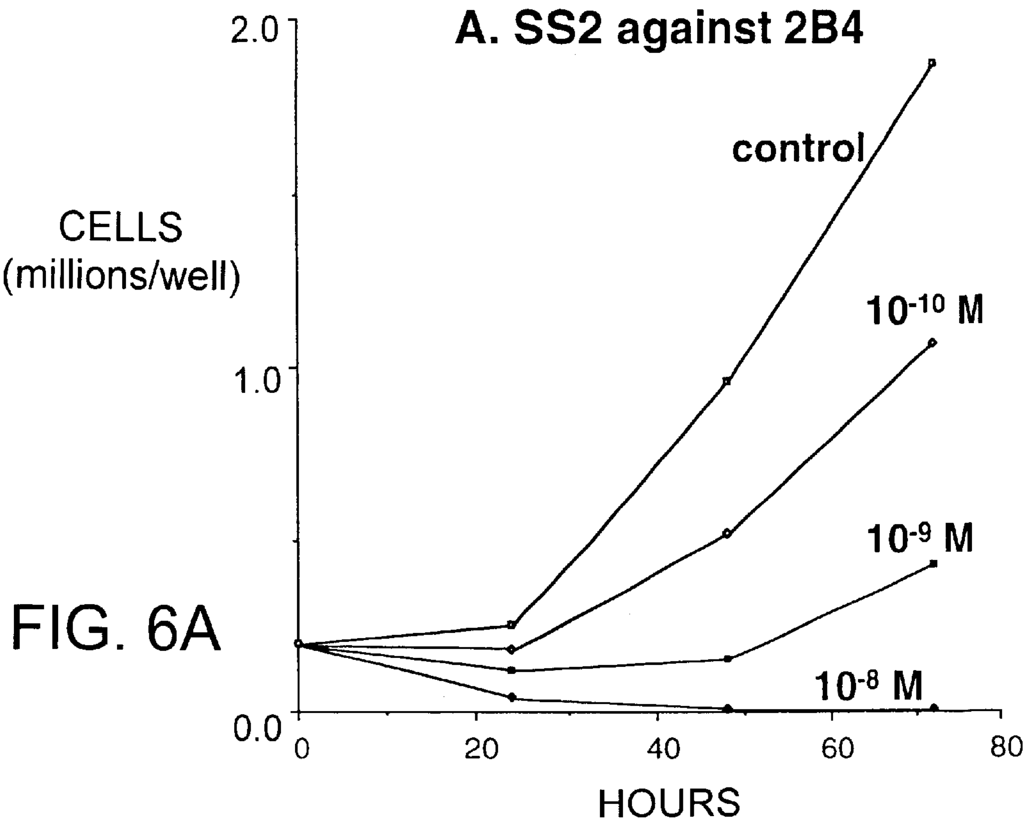
FIGS. 6A and 6C are line graphs showing the effect of the SS2 fraction on the in vitro proliferation and viability of CD3-expressing 2B4 T cell hybridoma cells (FIG. 6A) and CD3-non-expressing C1498 tumor cells (FIG. 6C).
Figure 6B:
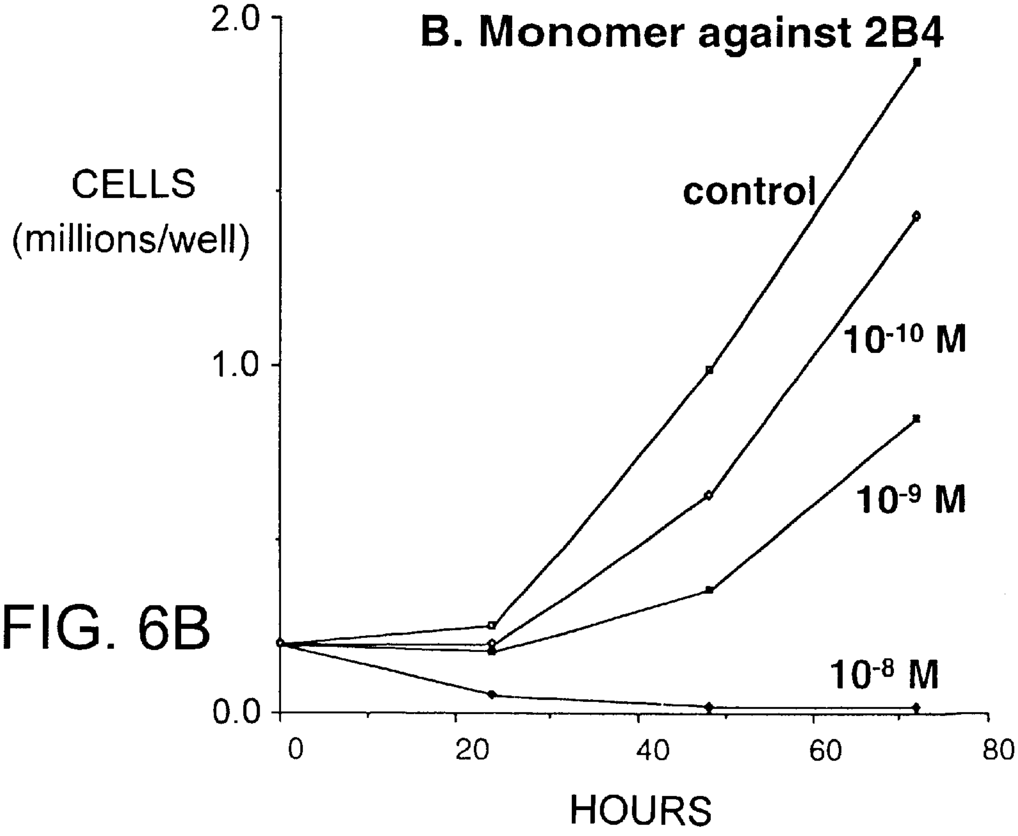
FIG. 6B is a line graph showing the effect in vitro of monomeric immunotoxin on the in vitro proliferation and viability of 2B4 cells.
Figure 6C:
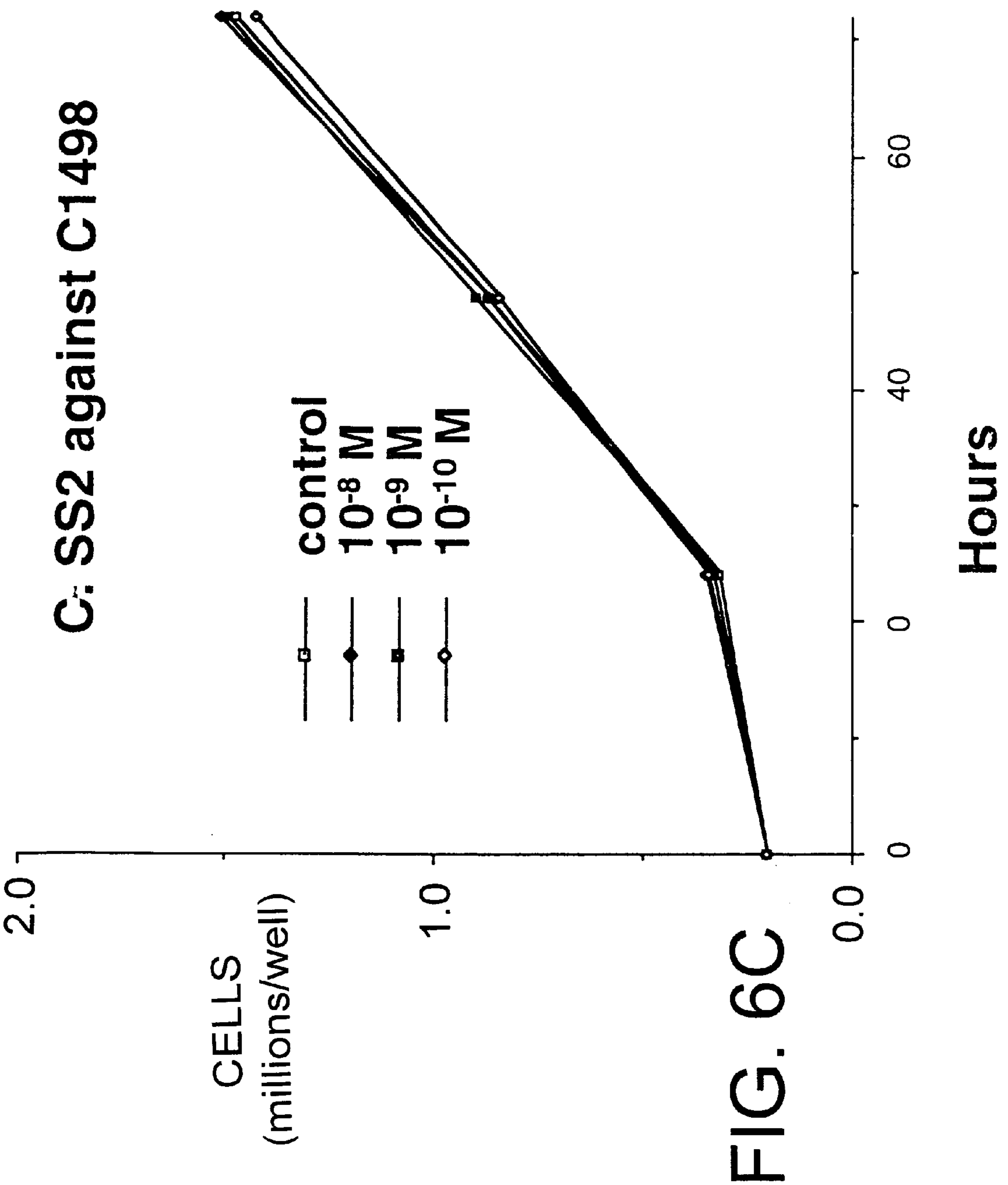

The in vitro cytotoxic activity of SS2 was also measured against the hybridoma T cell line 2B4. FIG. 6A shows that SS2 activity was dose dependent and all cells were killed at 10 nM SS2. FIG. 6B shows that the activity of the monomer was almost identical to that of SS2. FIG. 6C shows that SS2 had no inhibitory activity against the CD3—non-expressing C1498 cell line at any concentration tested.

In summary, the above in vitro studies indicated that SS2 was potent and highly selective in its activity against CD3-expressing cells. Since SS2 and monomer had nearly identical activity, intermolecular disulfide bonding did not sterically obstruct the binding or the catalytic activity of SS2.

Example 4

Determination of the Maximum in vivo Tolerated Dose (MTD) of SS2

To determine the MTD of SS2, it was injected BID into C57BL/6 mice (n=4–5/group) over a 4 day course. Administration of anti-CD3 recombinant antibody [Vallera et al. (1996) Blood 88:2342] and anti-CD3 monomeric immunotoxin [Vallera et al. (1995) Blood 86:4367] by this schedule was previously shown to induce a significant anti-GVHD effect. Table 2 shows that mice tolerated either 20 or 40 ug of the dimeric IT (SS2) per day. When the dose was increased to 80 ug/day, 1 mouse died on day 18, possibly of infectious complications. In contrast, all mice given 20 or 40 ug of monomeric immunotoxin per day died, and 1 mouse died in the group given 10 ug of monomeric immunotoxin per day. The monomeric immunotoxin ($DT_{390}$anti-CD3sFv) corresponded to the monomer from which the dimeric immunotoxin of SS2 was constructed. Thus, it contained the same 389 amino acids of DT linked to the same anti-CD3 sFv. In a separate experiment SS2 was given to bm12 mice. Groups of 3 mice given either 80 ug/day or 160 ug/day all survived. These data indicated that SS2 was at least 8-fold less toxic than monomer. Survivors were monitored for an additional 30 days with no signs of delayed toxic effects. There was a significant ($p<0.01$) difference between groups given 10 ug/day and 20–40 ug/day of monomer.

Example 5

In vivo Activity of SS2

An experiment was performed to determine whether SS2 had an effect on T cells in vivo. Splenocytes were removed from mice given SS2 BID (80 ug/day) for 5 days and stimulated in vitro with the T cell mitogen ConA. Table 3 shows greater than 77% reduction ($p=0.002$) in activity compared to control untreated mice. In contrast, there was a minimal and insignificant reduction in the number of B cells (measured by stimulating the same splenocytes with LPS).

TABLE 2

Determination of the maximum tolerated dose of SS2 in mice.

| Injected Immunotoxin | Dose (ug/day) | Number Alive/ Total Number Treated Day 10 | Day 20 | Day 30 |
|---|---|---|---|---|
| None | 0 | 5/5 | 5/5 | 5/5 |
| SS2 | 20 | 5/5 | 5/5 | 5/5 |
| SS2 | 40 | 5/5 | 5/5 | 5/5 |
| SS2 | 80 | 4/4 | 3/4 | 3/4 |
| monomer | 10 | 4/4 | 4/4 | 3/4 |
| monomer | 20 | 1/4 | 0/4 | 0/4 |
| monomer | 40 | 0/4 | 0/4 | 0/4 |

C57BL/6 mice were divided into groups (n = 4–5/group) and injected i.p. with varying concentrations of SS2 BID on days 0–3. Data are expressed as the number survivors/number of mice treated. Mice were observed for more than 30 additional days with no change in survival.

Flow cytometry studies were performed on splenocytes from the same mice. Table 4 shows that spleens from untreated mice contained 22% CD4 T cells and 15% CD8 T cells. SS2 significantly ($p=0.001$) reduced the proportion of CD4 cells by 95.6% and CD8 cells by 78.9%. The proportion of neither CD19 B cells nor myeloid (Mac-1+) cells was reduced.

TABLE 3

The effect of in vivo SS2 administration on T cell and B cell proliferation capacity

| | Mitogen activity CPM/well ConA | LPS |
|---|---|---|
| Untreated mouse | 13,921 ± 1,879 | 12,453 ± 806 |
| SS2-treated | 3,131 ± 1,224 | 10,723 ± 1,244 |
| % Change in activity | −77.5%* | −13.9% |
| p value | 0.002 | NS |

Groups of mice (n = 3–4/group) were given i.p. injections of SS2 (80 ug/day) BID Day 0–3. On day 4, splenocytes from treated or untreated control mice were tested for their ability to proliferate in response to the mitogens ConA and LPS using the [$^3$H]-thymidine incorporation assay. Spontaneous activity (activity in cells not stimulated with mitogen) was 1,260 ± 355 cpm.

TABLE 4

The effect of in vivo SS2 administration on the relative proportion of CD4+, CD8+, CD19+, and Mac-1+ cells

| | Flow cytometry % Fluorescent positive cells CD4 | CD8 | CD19 | Mac-1 |
|---|---|---|---|---|
| Untreated mouse | 22 ± 1 | 15 ± 1 | 56 ± 1 | 5 ± 2 |
| SS2-treated | 1 ± 1 | 4 ± 2 | 63 ± 8 | 36 ± 18 |
| % Change in activity | −95.6% | −78.9% | +12.5% | +720% |
| p value | 0.001 | 0.001 | NS | 0.039 |

Samples of the splenocytes described in Table 3 were tested for the expression of various cell surface markers by flow cytometry as described above.

To further study cells from mice treated with SS2, frozen tissue sections from SS2-treated (80 ug/day) mice were examined for the expression of various surface markers in situ. A splenic follicle was studied by immunohistochemistry and stained with H and E. A large number of mononuclear cells congregated around the central arteriole in the perivascular area of the white pulp. The majority of these cells were CD19 expressing B cells. As expected, the majority of myeloid cells (stained by antibody specific for Mac-1) were localized in the red pulp region. The majority of CD4 and CD8 expressing T cells were eliminated by SS2. In all, these data provided evidence that T cells are specifically targeted and killed in situ by the administration of SS2.

Example 6

Toxicity of SS2

The monomeric $DT_{390}$anti-CD3sFv immunotoxin was previously found to have relatively high kidney toxicity. To determine whether dimerization altered renal toxicity, tissue and serum were collected from mice treated in the same way as the mice in the experiment shown in Table 2. Microscopic examination of kidneys from mice given SS2 confirmed that at 80 ug/day SS2 was far less destructive to the kidney than monomer at 40 ug/day. After SS2 treatment (80 ug/day), kidney tissue looked almost normal with glomeruli, distal tubules, and proximal tubules intact. There was minimal infiltration with polymorphonuclear cells. All mice given this dosage were alive at 10 days. In contrast, monomer treatment severely damaged kidneys to the point that glomeruli disintegrated. Proximal tubules were destroyed and there were large areas of necrosis and infiltration, (predominantly mononuclear cell, but with some polymorphonuclear cells). Damage at this level was previously associated with a complete loss of function [Vallera et al. (1997) Protein Eng. 10:1071–1076]. As expected, these mice all died within 10 days. Only minor hepatic damage occurred in SS2-treated mice with minimal mononuclear cell infiltration. The same was true for monomer-treated mice.

Interestingly, we observed liver subcapsular infiltration that was more severe with SS2 treatment than with monomer treatment, perhaps related to the longer half-life of the SS2 molecule.

To determine whether SS2 had an effect on renal function, serum levels of BUN were measured (Table 5). There was no significant difference in BUN levels measured in mice given SS2 (80 ug/day ) compared to untreated mice indicating that the SS2 did not impair renal function. Precipitous increases in BUN levels were previously found to be induced by monomer administration [Vallera et al. (1997) Protein Eng. 10:1071–1076]. There was no difference in ALT levels with SS2 treatment indicating that hepatic function was also unaffected.

TABLE 5

| Kidney and Liver function after in vivo SS2 administration as measured by BUN and ALT function assays | | |
|---|---|---|
| Organ | BUN (mg/dL) | ALT (U/L) |
| Untreated | 19.3 ± 1.5 | 54.7 ± 14.6 |
| SS2-treated | 24.3 ± 5.7 | 54.0 ± 31.3 |

C57BL/6 mice were randomly grouped and injected with SS2 at 80 ug/day BID on days 0–3. On day 4 mice were bled and individual serum samples were studied for BUN and ALT levels. Data was averaged. Student t tests were performed comparing values from treated and untreated mice with no significant differences.

Example 7

Biodistribution of SS2 in the Kidney

To determine if there was a correlation between the decreased toxicity of SS2 and decreased localization in the kidney, SS2 was radiolabeled, injected into normal mice and its distribution in kidney, liver, and heart was studied. Table 6 shows that when SS2 and monomer were injected at equal doses, significantly ($p<0.002$) less SS2 (20.8%±2.3% injected dose/gram) accumulated in the kidney than did monomer (34.5%±6.4%). With respect to the liver, there was some increase in the accumulation of SS2 compared to monomer that was only a statistical trend ($p<0.067$). There was no difference in the amount of SS2 distributed in heart as compared to monomer. These biodistribution data correlated with histologic results and data from the functional studies reported above.

TABLE 6

| Biodistribution of SS2 and monomeric immunotoxin in kidney, liver, and heart tissue | | |
|---|---|---|
| | % Injected Dose/gram | |
| Organ | SS2 | Monomer |
| Kidney | 20.8* ± 2.3 | 34.5 ± 6.4 |
| Liver | 29.2~ ± 2.8 | 25.1 ± 3.3 |
| Heart | 4.1 ± 1.04 | 3.5 ± 0.5 |

SS2 and monomer were radiolabeled with $^{125}I$ and 2 uCi were injected i.v. into C57BL/6 mice (n = 5/group). After 30 minutes, organs were removed and counted for radioactivity. Data are presented as % injected dose/gram (mean ± 1 s.d. unit). Data obtained from the groups were compared using the Student's T test.
*p < 0.002 compared to monomer
~p = 0.067 compared to monomer

Example 8

SS2 Administration Prevents in vivo Lethal GVHD

To determine whether SS2 was able to protect against lethal GVHD and compare its activity to that of monomeric $DT_{390}$anti-CD3sFv, LN T cells from B6 mice were given to bm12 congenic irradiated (6 Gy) recipients to induce GVHD. A total of $10^6$ T cells (10 times greater than the lethal dose) were given to each recipient. In preparing the T cell fraction in the present experiment, passage over an Ig-column removed the contaminating 34% surface Ig expressing cells so that only 0.1 % contaminating Ig-expressing cells remained. All but 4% of the remaining cells expressed the αβ T cell receptor. This highly enriched T cell preparation, composed of 54% CD4+ cells and 37% CD8+ cells, killed a group of bm12 recipients in 20 days.

Figure 7A:
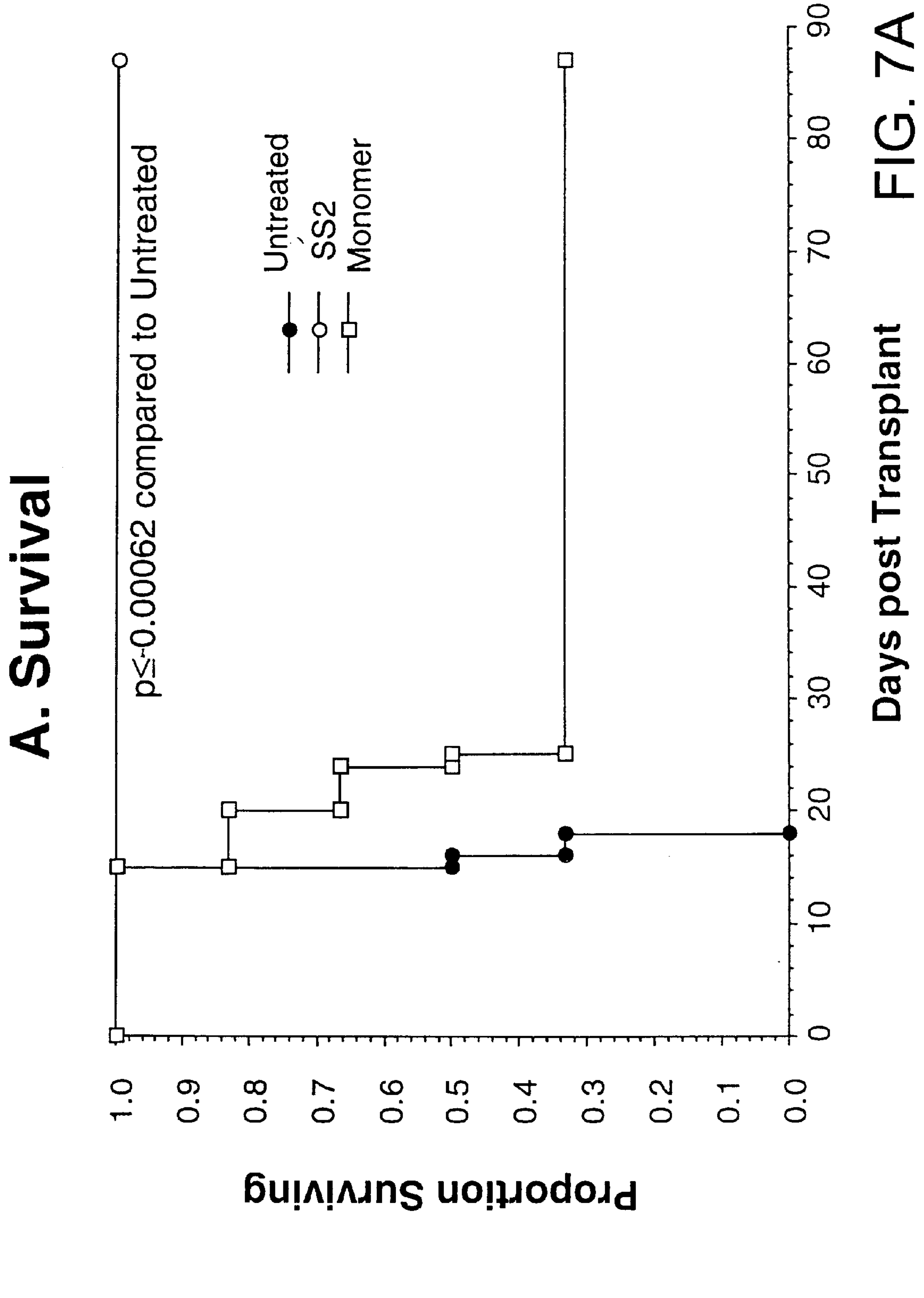
FIG. 7A depicts actuarial survival curves of irradiated bm12 mouse recipients of congenic C57BL/6 mouse T cells. The recipients were injected with no immunotoxin or with either the SS2 fraction or monomeric immunotoxin.
Figure 7B:
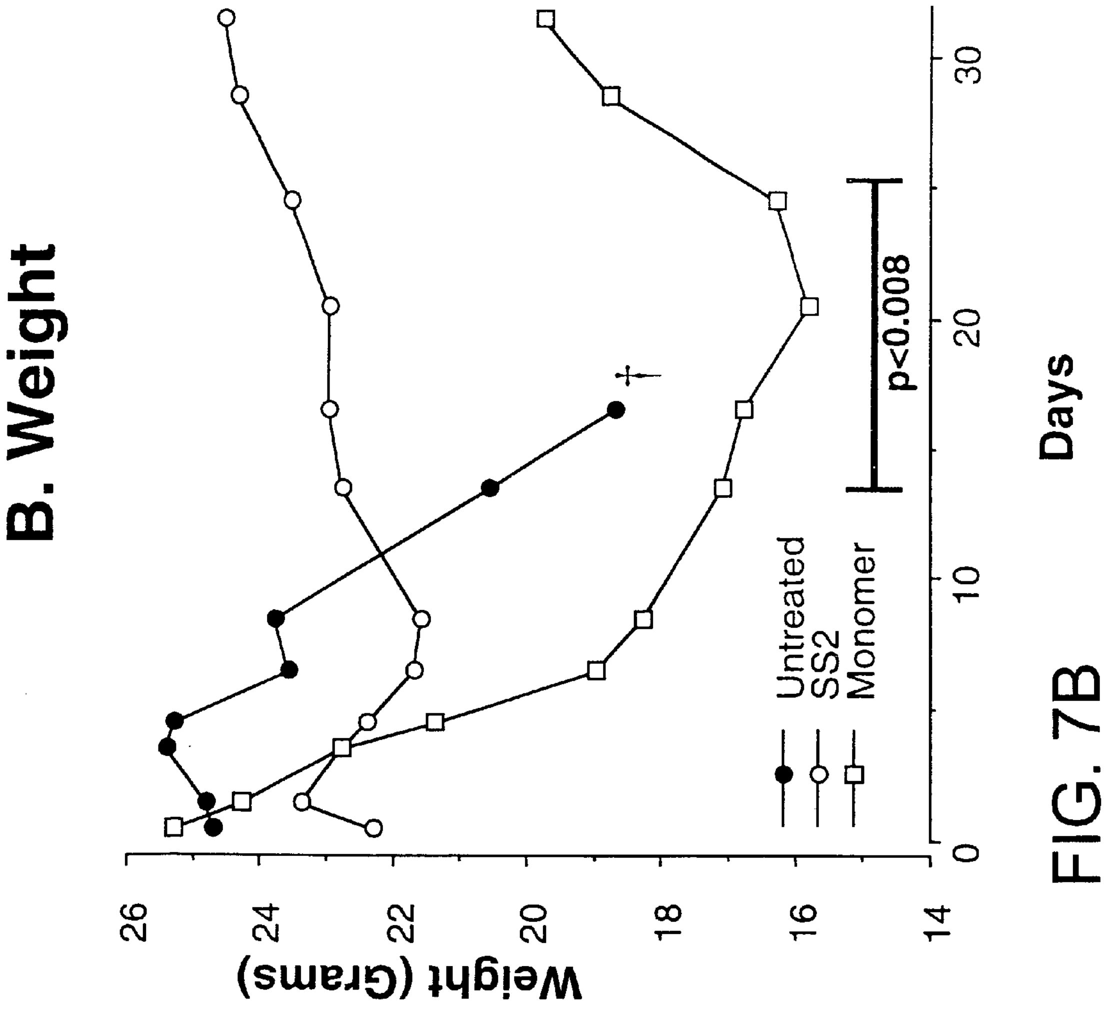
FIG. 7B is a line graph showing the change in weight over time of the mice depicted in FIG. 7A.

A cohort of six mice was injected i.v. with 10 ug of monomeric $DT_{390}$ anti-CD3sFv per day for 4 days, a dose based on the MTD determined from the data in Table 2. Four of these mice died (FIG. 7A). The weight data for mice shown in FIG. 7B indicated that the deaths were GVHD-related in that all these animals showed precipitous weight loss (over 25% of pre-transplant body weight) and death occurred on days 19–26. Deaths were not due to toxicity since toxicity deaths occur before day 5 and do not involve significant weight loss. Although mice tolerated a 4 day injection schedule of dimeric immunotoxin given BID, the administration of only 2 injections of SS2 over the course of 1 day (totaling 40 ug) was sufficient to protect all mice from lethal GVHD (FIG. 7A). This dose was well below the MTD. In a separate experiment, in which a cohort of untransplanted normal bm12 mice were given 160 ug/day SS2, all mice lived indicating the presence of a therapeutic window in which the therapeutic dose of 40 ug given in a single day was at least 4-fold lower than a MTD of 160 ug given in a single day. No such therapeutic window was observed with monomeric immunotoxin which did not prevent GVHD in the "B6 into bm12" model at its MTD of 10 ug/day BID given over the course of 4 days.

Although the invention has been described with reference to the presently preferred embodiment, it should be understood that various modifications can be made without departing from the spirit of the invention. Accordingly, the invention is limited only by the following claims.

What is claim is:

1. A fusion protein molecule comprising a toxic domain, a targeting domain, and at least one heterologous coupling moiety, wherein cysteine residues forming disulfide bonds within said fusion protein are:

(i) cysteine residues native to the toxic domain and form disulfide bonds within the toxic domain; or (ii) cysteine residues native to the targeting domain and form disulfide bonds within the targeting domain, and wherein the at least one heterologous coupling moiety is a moiety through which a second fusion protein molecule can be bound to the fusion protein molecule.

2. A multimeric immunotoxic protein comprising at least two fusion protein monomers, wherein each fusion protein monomer:

comprises a targeting domain and a toxic domain; and is physically associated with the other fusion protein monomers, wherein said targeting domain binds to a target molecule on a target cell, and if a targeting domain is an antibody fragment, said antibody fragment has fewer than fourteen immunoglobulin heavy chain constant region amino acid residues, wherein an antibody fragment with no immunoglobulin heavy chain constant region amino acid residues has one VH chain and one VL chain.

3. The multimeric immunotoxic protein of claim 2, wherein each of said fusion protein monomers further comprises one or more coupling moieties and the physical association of the fusion protein monomer is by at least one of the one or more coupling moieties.

4. The multimeric immunotoxic protein of claim 3, wherein the coupling moiety is a terminal moiety.

5. The multimeric immunotoxin protein of claim 4, wherein the terminal moiety is a C-terminal moiety.

6. The multimeric immunotoxic protein of claim 3, wherein the one or more coupling moieties are cysteine residues.

7. The multimeric immunotoxic protein of claim 3, wherein at least one of the one or more coupling moieties is a heterologous coupling moiety.

8. The multimeric immunotoxic protein of claim 2, wherein each of the fusion protein monomers comprises the same amino acid sequence.

9. The multimeric immunotoxic protein of claim 8, wherein the targeting domain is an antibody fragment.

10. The multimeric immunotoxic protein of claim 9, wherein the antibody fragment is a single chain Fv (sFv).

11. The multimeric immunotoxic protein of claim 10, wherein the sFv binds to a target molecule on a T cell.

12. The multimeric immunotoxic protein of claim 11, wherein the target molecule is a CD3 polypeptide.

13. The multimeric immunotoxic protein of claim 2, wherein the targeting domain is a targeting polypeptide selected from the group consisting of: (a) a cytokine; (b) a ligand for a cell adhesion receptor; (c) a ligand for a signal transduction receptor; (d) a hormone; (e) a molecule that binds to a death domain family molecule; (f) an antigen; and (g) a functional fragment of any of (a)–(f).

14. The multimeric immunotoxic protein of claim 2, wherein the toxic domain is a toxic polypeptide selected from the group consisting of: (a) ricin, (b) Pseudomonas exotoxin (PE); (c) bryodin; (d) gelonin; (e) α-sarcin; (f) aspergillin; (g) restrictocin; (h) angiogenin; (i) saporin; (j) abrin; (k) pokeweed antiviral protein (PAP); and (l) a functional fragment of any of (a)–(k).

15. The multimeric immunotoxic protein of claim 2, wherein the toxic domain is diphtheria toxin (DT) or a functional fragment thereof.

16. The multimeric immunotoxic protein of claim 15, wherein the toxic domain comprises amino acids 1-389 of DT.

17. The multimeric immunotoxic protein of claim 2, wherein the target cell is in a mammal.

18. The multimeric immunotoxic protein of claim 17, wherein the mammal is suspected of having graft-versus-host disease (GVHD).

19. The multimeric immunotoxic protein of claim 18, wherein the target molecule is CD3.

20. The multimeric immunotoxic protein of claim 2, wherein the target cell is a cancer cell.

21. The multimeric immunotoxic protein of claim 20, wherein the cancer sell is selected from the group consisting of a neural tissue cancer cell, a melanoma cell, a breast cancer cell, a lung cancer cell, a gastrointestinal cancer cell, an ovarian cancer cell, a testicular cancer cell, a lung cancer cell, a prostate cancer cell, a cervical cancer cell, a bladder cancer cell, a vaginal cancer cell, a liver cancer cell, a renal cancer cell, a bone cancer cell, and a vascular tissue cancer cell.

22. A multimeric immunotoxic protein comprising at least two fusion protein molecules of claim 1, each fusion protein molecule being bound by at least one of the heterologous coupling moieties to one or more of other said fusion protein molecules.

23. The multimeric immunotoxic protein of claim 22, wherein the at least one heterologous coupling moiety is a cysteine residue.

24. The multimeric immunotoxic protein of claim 22, wherein the targeting domain is an antibody fragment.

25. The multimeric immunotoxic protein of claim 24, wherein the antibody fragment is a sFv.

26. The multimeric immunotoxic protein of claim 25, wherein the sFv binds to a CD3 polypeptide.

27. The multimeric immunotoxic protein of claim 22, wherein the toxic domain is diphtheria toxin (DT) or a functional fragment thereof.

28. The multimeric immunotoxic protein of claimed 27 wherein the toxic domain comprises amino acids 1-389 of DT.

* * * * *

UNITED STATES PATENT AND TRADEMARK OFFICE

CERTIFICATE OF CORRECTION

PATENT NO. : 6,492,498 B1 Page 1 of 1
DATED : December 10, 2002
INVENTOR(S) : Daniel A. Vallera and Bruce R. Blazar It is certified that error appears in the above-identified patent and that said Letters Patent is hereby corrected as shown below:

Column 1,
Line 4, replace "R10" with -- R01 --

Column 9,
Line 28, replace "See" with -- See --

Column 16,
Line 42, delete "Age"

Column 21,
Lines 46 and 47, replace "37ºC." with -- 37º C --

Column 22,
Line 15, replace "40ºC." with -- 40ºC --
Line 15, replace "LIN" with -- LN --

Signed and Sealed this

Eighth Day of July, 2003

JAMES E. ROGAN
*Director of the United States Patent and Trademark Office*

SEQUENCE LISTING

```
<160> NUMBER OF SEQ ID NOS:  6

<210> SEQ ID NO 1
<211> LENGTH: 25
<212> TYPE: PRT
<213> ORGANISM: Homo sapiens

<400> SEQUENCE: 1

Met Ala Ile Ser Gly Val Pro Val Leu Gly Phe Phe Ile Ile Ala Val
  1               5                  10                  15

Leu Met Ser Ala Gln Glu Ser Trp Ala
             20                  25
```

-continued

```
<210> SEQ ID NO 2
<211> LENGTH: 4
<212> TYPE: PRT
<213> ORGANISM: Rattus rattus

<400> SEQUENCE: 2

Lys Asp Glu Leu
  1


<210> SEQ ID NO 3
<211> LENGTH: 5
<212> TYPE: PRT
<213> ORGANISM: Artificial Sequence
<220> FEATURE:
<223> OTHER INFORMATION: Synthetically generated peptides

<400> SEQUENCE: 3

Ala Ser Gly Gly Pro
  1               5


<210> SEQ ID NO 4
<211> LENGTH: 15
<212> TYPE: PRT
<213> ORGANISM: Artificial Sequence
<220> FEATURE:
<223> OTHER INFORMATION: Synthetically generated peptides

<400> SEQUENCE: 4

Gly Gly Gly Gly Ser Gly Gly Gly Gly Ser Gly Gly Gly Gly Ser
  1               5                  10                  15


<210> SEQ ID NO 5
<211> LENGTH: 33
<212> TYPE: DNA
<213> ORGANISM: Artificial Sequence
<220> FEATURE:
<223> OTHER INFORMATION: Synthetically generated oligonucleotides

<400> SEQUENCE: 5

agatattcca tgggcgctga tgatgttgtt gat                                  33


<210> SEQ ID NO 6
<211> LENGTH: 24
<212> TYPE: DNA
<213> ORGANISM: Artificial Sequence
<220> FEATURE:
<223> OTHER INFORMATION: Synthetically generated oligonucleotides

<400> SEQUENCE: 6

aagcttttac taacaggaga cggt                                            24
```